US011330978B2

(12) United States Patent
Horino et al.

(10) Patent No.: US 11,330,978 B2
(45) Date of Patent: May 17, 2022

(54) SUBJECTIVE OPTOMETRY APPARATUS, SUBJECTIVE OPTOMETRY METHOD, AND RECORDING MEDIUM STORING SUBJECTIVE OPTOMETRY PROGRAM

(71) Applicant: NIDEK CO., LTD., Aichi (JP)

(72) Inventors: Taeko Horino, Aichi (JP); Michihiro Takii, Aichi (JP); Noriji Kawai, Aichi (JP)

(73) Assignee: NIDEK CO., LTD., Aichi (JP)

( * ) Notice: Subject to any disclaimer, the term of this patent is extended or adjusted under 35 U.S.C. 154(b) by 829 days.

(21) Appl. No.: 15/865,799

(22) Filed: Jan. 9, 2018

(65) Prior Publication Data

US 2018/0192867 A1 Jul. 12, 2018

(30) Foreign Application Priority Data

Jan. 12, 2017 (JP) ............................ JP2017-003232

(51) Int. Cl.
*A61B 3/028* (2006.01)
*A61B 3/103* (2006.01)
(Continued)

(52) U.S. Cl.
CPC ............ *A61B 3/0285* (2013.01); *A61B 3/032* (2013.01); *A61B 3/0325* (2013.01); *A61B 3/06* (2013.01);
(Continued)

(58) Field of Classification Search
CPC ....... A61B 3/032; A61B 3/0033; A61B 3/028; A61B 3/0041; A61B 3/0091; A61B 3/02;
(Continued)

(56) References Cited

U.S. PATENT DOCUMENTS

| | | | | |
|---|---|---|---|---|
| 2008/0151188 A1 | 6/2008 | Kawai et al. | | |
| 2012/0287398 A1* | 11/2012 | Baker | A61B 3/103 | 351/201 |
| 2015/0342454 A1* | 12/2015 | Foster | A61B 3/103 | 351/211 |

FOREIGN PATENT DOCUMENTS

| | | |
|---|---|---|
| JP | 63-502642 A | 10/1988 |
| JP | 4-40935 A | 2/1992 |

(Continued)

OTHER PUBLICATIONS

Japanese Office Action (JPOA) dated Nov. 17, 2020 for the corresponding Japanese Patent Application No. 2017-003232 and its English translation.

(Continued)

*Primary Examiner* — Collin X Beatty
*Assistant Examiner* — Grant A Gagnon
(74) *Attorney, Agent, or Firm* — Rankin, Hill & Clark LLP

(57) ABSTRACT

A subjective optometry apparatus includes: a subjective measurer which has a corrective optical system disposed on an optical path of a light projecting optical system configured to project a target light flux toward an examinee's eye and configured to change an optical characteristic of the target light flux and which is configured to subjectively measure an optical characteristic of the examinee's eye; an acquisitor configured to acquire position information on at least one of examinee's right and left eyes; a determiner configured to determine, based on the position information acquired by the acquisitor, whether or not subjective measurement can be implemented in a binocular open state of the examinee's right and left eyes, thereby acquiring deter- (Continued)

mination information; and a determination information output unit configured to output the determination information acquired by the determiner.

16 Claims, 11 Drawing Sheets

(51) Int. Cl.

| | |
|---|---|
| ***A61B 3/032*** | (2006.01) |
| ***A61B 3/06*** | (2006.01) |
| *A61B 3/00* | (2006.01) |
| *A61B 3/036* | (2006.01) |

(52) U.S. Cl.
CPC ............ *A61B 3/103* (2013.01); *A61B 3/0025* (2013.01); *A61B 3/0041* (2013.01); *A61B 3/0075* (2013.01); *A61B 3/036* (2013.01)

(58) Field of Classification Search
CPC ....... A61B 3/0025; A61B 3/022; A61B 3/024; A61B 3/036; A61B 3/08; A61B 3/103; A61B 3/063; A61B 3/1015; A61B 3/005; A61B 3/0083; A61B 3/06; A61B 3/066; A61B 3/09; A61B 3/18; A61B 5/16; A61B 3/0008; A61B 3/0058; A61B 3/0075; A61B 3/0285; A61B 5/163; A61B 5/7475; A61B 3/0016; A61B 3/04; A61B 3/10; A61B 3/1035; A61B 3/112; A61B 3/113; A61B 3/12; A61B 3/14; A61B 5/0002; A61B 5/1036; A61B 5/161; A61B 5/162; A61B 5/4088; A61B 13/00; A61B 2560/0431; A61B 3/111; A61B 3/1176; A61B 3/185; A61B 5/0066; A61B 5/0068; A61B 5/0484; A61B 5/055; A61B 5/165; A61B 5/40; A61B 5/4011; A61B 5/4017; A61B 5/4064; A61B 5/4082; A61B 5/4824; A61B 5/4848; A61B 5/6814; A61B 5/749
USPC .......................................................... 351/239
See application file for complete search history.

(56) References Cited

FOREIGN PATENT DOCUMENTS

| | | | |
|---|---|---|---|
| JP | H05176893 | A | 7/1993 |
| JP | 7-222717 | A | 8/1995 |
| JP | 9-47430 | A | 2/1997 |
| JP | 2002-83156 | A | 3/2002 |
| JP | 2002-209850 | A | 7/2002 |
| JP | 2004-166903 | A | 6/2004 |
| JP | 2008-161218 | A | 7/2008 |
| WO | 87/02565 | A1 | 5/1987 |

OTHER PUBLICATIONS

Japanese Office Action (JPOA) dated Aug. 31, 2021 for corresponding Japanese Patent Application No. 2017-003232 and its English translation.

* cited by examiner

SUBJECTIVE OPTOMETRY APPARATUS, SUBJECTIVE OPTOMETRY METHOD, AND RECORDING MEDIUM STORING SUBJECTIVE OPTOMETRY PROGRAM

CROSS-REFERENCE TO RELATED APPLICATION

This application claims priority from Japanese Patent Application No. 2017-003232 filed with the Japan Patent Office on Jan. 12, 2017, the entire content of which is hereby incorporated by reference.

BACKGROUND

1. Technical Field

The present disclosure relates to a subjective optometry apparatus, a subjective optometry method, and a recording medium storing a subjective optometry program.

2. Description of the Related Art

In a known subjective optometry apparatus (see JP-A-05-176893), an eye refractive power measurement unit disposed in front of an examinee's eye is used. An optical element such as a spherical lens or a cylindrical (astigmatic) lens is disposed at an examination window of the eye refractive power measurement unit. A target is presented to the examinee's eye through the disposed optical element. In this way, the refractive power etc. of the examinee's eye is examined (measured).

In corrected refractive power examination by the subjective optometry apparatus of this type, the right and left eyes are separately examined. The examination target is, through the optical element disposed at the examination window, presented to the eye (hereinafter referred to as a "measurement target eye") to be examined. A covering plate provided at one of rotary discs is disposed at the examination window corresponding to the eye (hereinafter referred to as an "unmeasured eye") not to be examined. Thus, the examination target is not presented to the unmeasured eye.

A method in which no covering plate is disposed on an unmeasured eye side has been also known. In this method, the unmeasured eye is fogged by addition of a positive spherical power or use of a deflecting mirror. Then, examination under a binocular open state is implemented. It has been assumed that a measurement result in a state closer to natural vision is obtained by such examination in the binocular open state.

SUMMARY

A subjective optometry apparatus includes: a subjective measurer which has a corrective optical system disposed on an optical path of a light projecting optical system configured to project a target light flux toward an examinee's eye and configured to change an optical characteristic of the target light flux and which is configured to subjectively measure an optical characteristic of the examinee's eye; an acquisitor configured to acquire position information on at least one of examinee's right and left eyes; a determiner configured to determine, based on the position information acquired by the acquisitor, whether or not subjective measurement can be implemented in a binocular open state of the examinee's right and left eyes, thereby acquiring determination information; and a determination information output unit configured to output the determination information acquired by the determiner.

DESCRIPTION OF THE EMBODIMENTS

Figure 1:
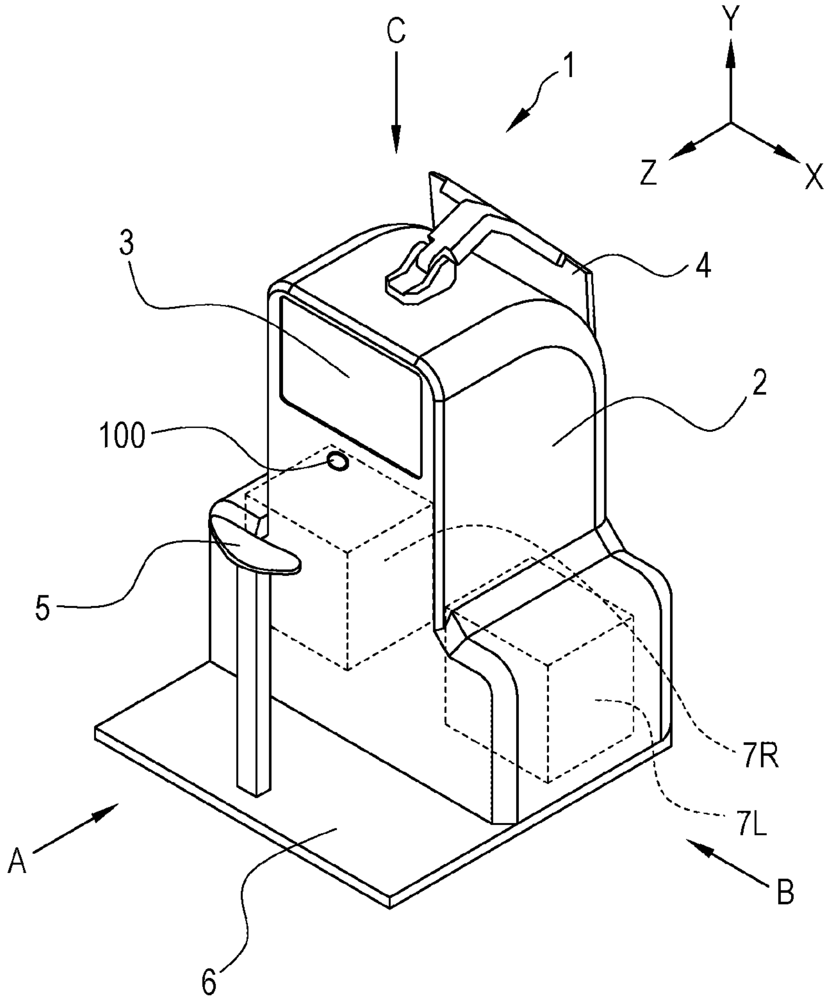
FIG. 1 is an external view of a subjective optometry apparatus according to one example of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Subjective examination in a binocular open state by means of a subjective optometry apparatus is sometimes performed for an examinee (e.g., an examinee with heterotropia) who is difficult to obtain favorable fusion by both eyes. In this case, subjective examination is performed in a state in which the examinee is difficult to obtain favorable fusion by both eyes. For this reason, it is difficult to accurately perform examination. That is, in examination for the examinee with heterotropia, the visual line direction of an unmeasured eye might direct a position different from a target, for example. In this case, subjective examination is performed in a state in which the examinee is difficult to obtain favorable fusion by both eyes. For this reason, it is difficult to accurately perform measurement.

One object of the present disclosure is to provide a subjective optometry apparatus, a subjective optometry method, and a recording medium storing a subjective optometry program so that subjective examination can be accurately and easily performed.

A subjective optometry apparatus according to an aspect of the present disclosure (the present optometry apparatus) includes: a subjective measurer which has a corrective optical system disposed on an optical path of a light projecting optical system configured to project a target light flux toward an examinee's eye and configured to change an optical characteristic of the target light flux and which is configured to subjectively measure an optical characteristic of the examinee's eye; an acquisitor configured to acquire position information on at least one of examinee's right and left eyes; a determiner configured to determine, based on the position information acquired by the acquisitor, whether or not subjective measurement can be implemented in a binocular open state of the examinee's right and left eyes, thereby acquiring determination information; and a determination information output unit configured to output the determination information acquired by the determiner.

The present optometry apparatus may further include: a setter configured to receive the determination information output by the determination information output unit and set, based on the determination information, a measurement mode either to a covering mode for performing subjective examination for one of the examinee's right and left eyes with the other eye being covered or to a binocular open mode for performing subjective examination for one eye in the binocular open state; and a drive controller configured to control the subjective measurer in accordance with the measurement mode set by the setter.

In the present optometry apparatus, the determiner may acquire a determination result as the determination information.

In the present optometry apparatus, the determiner may be configured to acquire guide information as the determination information, and the guide information is information for guiding an examiner to the measurement mode of either the covering mode for performing subjective examination for one of the examinee's right and left eyes with the other eye being covered or the binocular open mode for performing subjective examination for one eye in the binocular open state.

In the present optometry apparatus, the determination information output unit may display the determination information on a display.

The present optometry apparatus may further include an anterior segment acquisitor configured to acquire an anterior segment image of at least one of the examinee's right and left eyes, and the acquisitor may acquire the position information by analyzing the anterior segment image.

In this case, the anterior segment acquisitor may acquire a first anterior segment image as the anterior segment image of at least one of the examinee's right and left eyes in a case where both of the examinee's right and left eyes are in an uncovered state, and acquires a second anterior segment image as the anterior segment image of at least one of the examinee's right and left eyes in a case where the other eye is in a covered state, and the acquisitor may acquire the position information by analyzing the first anterior segment image and the second anterior segment image.

The acquisitor may detect a pupil position of the examinee's eye by performing analysis processing for the anterior segment image and may acquire the position information based on the pupil position.

In the present subjective optometry apparatus, the corrective optical system may have a right-left pair of an examinee's right-eye corrective optical system and an examinee's left-eye corrective optical system, the examinee's right-eye corrective optical system and the examinee's left-eye corrective optical system may be configured to be position-adjusted to the examinee's right and left eyes, respectively, and the acquisitor may detect at least any one of first position information as position information on the examinee's right-eye corrective optical system obtained when the examinee's right-eye corrective optical system is position-adjusted to the right examinee's eye and second position information as position information on the examinee's left-eye corrective optical system obtained when the examinee's left-eye corrective optical system is position-adjusted to the left examinee's eye, and may acquire the position information on the examinee's eye based on at least any of the detected first position information and the detected second position information.

A recording medium storing a subjective optometry program according to an aspect of the present disclosure records the subjective optometry program executed by a processor of a subjective optometry apparatus to cause the subjective optometry apparatus to execute acquiring position information on at least one of examinee's right and left eyes, determining, based on the position information, availability of binocular fusion by the examinee's right and left eyes to acquire determination information, and outputting the determination information.

A subjective optometry method according to an aspect of the present disclosure includes: acquiring position information on at least one of examinee's right and left eyes; determining, based on the position information, availability of binocular fusion by the examinee's right and left eyes to acquire determination information; outputting the determination information; and subjectively measuring an optical characteristic of each of the examinee's eyes.

Hereinafter, a typical embodiment will be described with reference to the drawings. FIGS. 1 to 13 are views for describing a subjective optometry apparatus and a subjective optometry program according to the present embodiment. Note that the technique of the present disclosure is not limited to the apparatus described in the present embodiment. For example, terminal control software (a program) for performing the functionality of the embodiment below may be supplied to a system or an apparatus via a network, various storage media, etc. In addition, a control apparatus (e.g., a CPU) of this system or apparatus may be configured to read and execute the above-described program.

In description below, the front-rear direction of the subjective optometry apparatus will be referred to as a "Z-direction." The horizontal direction (the right-left direction) in a plane perpendicular to the front-rear direction will be referred to as an "X-direction." Further, the vertical direction (the up-down direction) in the plane perpendicular to the front-rear direction will be referred to as a "Y-direction." Note that "L" and "R" to reference signs indicate use for the left eye and the right eye, respectively.

<Outline>

For example, in the present embodiment, the subjective optometry apparatus (e.g., a subjective optometry apparatus 1) includes a subjective measurer, and is configured to subjectively measure optical characteristics of an examinee's eye. For example, the subjective measurer has a light projecting optical system (e.g., a light projecting optical system 30) and a corrective optical system (e.g., a corrective optical system 60). For example, the light projecting optical system is configured to project a target light flux toward the examinee's eye. For example, the corrective optical system is disposed on the optical path of the light projecting optical system to change optical characteristics of the target light flux.

For example, the light projecting optical system has a light source (e.g., a display 31) configured to irradiate the target light flux. Moreover, the light projecting optical system may have, for example, at least one or more optical members configured to guide the target light flux toward the examinee's eye, the target light flux being projected from the light source configured to project the target light flux.

For example, a display (e.g., the display 31) may be used as the light source configured to project the target light flux. For example, a liquid crystal display (LCD) or an organic electro luminescence (EL) is used as the display. For example, an examination target such as a Landolt ring target is displayed on the display. Alternatively, a digital micro-mirror device (DMD) may be, for example, used as the light source configured to project the target light flux. Generally, the DMD has high reflectivity, and is bright. Thus, as compared to the case of using a display (a liquid crystal display) using polarization, the amount of light of the target light flux can be maintained. The light source configured to project the target light flux may also have, for example, a visible light source for target presentation and a target plate. In this case, the target plate is a rotatable disc plate with a plurality of targets, for example. The plurality of targets includes a visual acuity examination target used for subjective measurement, for example. For example, a target for each visual acuity value (targets corresponding to visual acuity values of 0.1, 0.3, . . . , and 1.5) is prepared as the visual acuity examination target. For example, the targets are switchably disposed on the optical path for guiding the target light flux to the examinee's eye as the target plate is rotated by means of a motor etc. Needless to say, light sources with other configurations than above may be used as the light source configured to project the target light flux.

For example, the light projecting optical system may have a right-left pair of a right-eye light projecting optical system and a left-eye light projecting optical system. For example, the members forming the right-eye light projecting optical system and the members forming the left-eye light projecting optical system may be identical to each other. Alternatively, at least some of the members may be different between the right-eye light projecting optical system and the left-eye light projecting optical system, for example. For example, at least some of members may be used commonly for the right-eye light projecting optical system and the left-eye light projecting optical system. Alternatively, the members forming the right-eye light projecting optical system and the members forming the left-eye light projecting optical system may be separately provided.

For example, the corrective optical system may be configured to change the optical characteristics (at least any of e.g., a spherical power, a cylindrical diopter power, a cylindrical axis, a polarization characteristic, and an amount of aberration) of the target light flux. For example, the corrective optical system may be configured to control the optical element to change the optical characteristics of the target light flux. For example, at least any of a spherical lens, a cylindrical lens, a cross cylinder lens, a rotary prism, a wavefront modulation element, etc. may be used as the optical element. Needless to say, an optical element different from the above-described optical elements may be used as the optical element, for example.

For example, the corrective optical system may be configured to optically change the presentation position (the presenting distance) of the target with respect to the examinee's eye, thereby correcting the spherical power of the examinee's eye. In this case, the corrective optical system may be, for example, configured to move the light source (e.g., the display) in an optical axis direction to optically change the presentation position (the presenting distance) of the target. Alternatively, the corrective optical system may be configured to move, in the optical axis direction, the optical element (e.g., the spherical lens) disposed on the optical path, for example. Needless to say, the corrective optical system may be a combination of the member configured to control the optical element and the member configured to move, in the optical axis direction, the optical element disposed on the optical path.

For example, the corrective optical system may be an optometry unit (a phoropter) configured to switch the optical element disposed in front of the examinee's eye. For example, the optometry unit may have a lens disc including a plurality of optical elements disposed on the same circumference and a driver configured to rotate the lens disc. Further, the optometry unit may be configured to electrically switch the optical element by driving of the driver (e.g., a motor).

For example, the corrective optical system may have an optical element disposed between the optical member configured to guide the target light flux from the light projecting optical system to the examinee's eye and a target presenter. Further, the corrective optical system may be configured to control the optical element to change the optical characteristics of the target light flux. That is, the corrective optical system (a corrector) may be configured similar to a phantom lens refractometer (a phantom corrective optical system). In this case, the target light flux corrected by the corrective optical system is guided to the examinee's eye through the optical member, for example.

For example, the corrective optical system may have a right-left pair of an examinee's right-eye corrective optical system and an examinee's left-eye corrective optical system. In this case, the corrective optical system may include, for example, an optical member shared by a right-eye optical path including the right-eye corrective optical system and a left-eye optical path including the left-eye corrective optical system, the optical member guiding the target light flux corrected by the corrective optical system to the examinee's eye.

For example, the subjective optometry apparatus includes an acquisitor (e.g., a controller 70). For example, the acquisitor is configured to acquire position information on at least one of the examinee's right and left eyes. For example, the acquisitor may acquire the position information on at least one of the examinee's right and left eyes in a case where both of the examinee's right and left eyes are in an uncovered state. Further, the acquisitor may acquire the position information on at least one of the examinee's right and left eyes in a case where one of the examinee's eyes is in a covered state.

For example, the subjective optometry apparatus includes a determiner (e.g., the controller 70). For example, the determiner is configured to determine, based on the position information acquired by the acquisitor, whether or not subjective measurement can be implemented in the binocular open state of the examinee's right and left eyes, thereby acquiring determination information. For example, the subjective optometry apparatus includes a determination information output unit. For example, the determination information output unit (e.g., the controller 70) is configured to output the determination information acquired by the determiner.

For example, the subjective optometry apparatus in the present embodiment includes the acquisitor configured to acquire the position information on at least one of the examinee's right and left eyes, the determiner configured to determine whether or not subjective measurement can be implemented in the binocular open state of the examinee's right and left eyes to acquire the determination information, and the determination information output unit configured to output the determination information. Thus, an examiner refers to the output determination information so that subjective measurement can be performed after determination on whether or not binocular open examination for the examinee's eyes is to be implemented has been easily made even when the examiner is unaccustomed to examination.

Note that in the present embodiment, at least two or more members of the acquisitor, the determiner, and the determination information output unit may be configured as a single member. Needless to say, the acquisitor, the determiner, and the determination information output unit may be configured as multiple (separate) members.

For example, the subjective optometry apparatus may include a setter (e.g., the controller 70). For example, the setter is configured to receive the determination information output by the determination information output unit to set, based on the determination information, a measurement mode either to the covering mode for performing subjective examination for one of the examinee's right and left eyes with the other eye being covered or to the binocular open mode for performing subjective examination for one eye in the binocular open state. In this case, the subjective optometry apparatus may include a drive controller configured to control the subjective measurer in accordance with the measurement mode set by the setter, for example.

For example, the subjective optometry apparatus receives the determination information output from the determination information output unit, thereby setting, based on the determination information, the measurement mode either to the covering mode for performing subjective examination for one of the examinee's right and left eyes with the other eye being covered or to the binocular open mode for performing subjective examination for one eye in the binocular open state. Moreover, the subjective optometry apparatus in the present embodiment includes the drive controller configured to control the subjective measurer in accordance with the set mode. With this configuration, a proper measurement mode is set in accordance with the state of binocular vision by the examinee's eyes. Thus, the probability of selecting an erroneous measurement mode by the examiner is reduced, and therefore, subjective measurement can be accurately performed.

<Acquisitor>

For example, the acquisitor may be configured to analyze an anterior segment image to acquire the position information. In this case, the subjective optometry apparatus may include an anterior segment acquisitor (e.g., an anterior segment imaging optical system 100, the controller 70) configured to acquire the anterior segment image of at least one of the examinee's right and left eyes, for example. Note that the anterior segment acquisitor may be configured to receive an anterior segment image photographed by an imaging optical system of an apparatus different from the subjective optometry apparatus, thereby acquiring the anterior segment image, for example. For example, the subjective optometry apparatus in the present embodiment includes the anterior segment acquisitor configured to acquire the anterior segment image of at least one of the examinee's right and left eyes. Moreover, the subjective optometry apparatus in the present embodiment analyzes the anterior segment image acquired by the anterior segment acquisitor, thereby acquiring the position information. With this configuration, the examiner can easily obtain the position information on the examinee's eye based on the anterior segment image of the examinee's eye. Moreover, the examiner can easily determine (acquire) movement of the visual line direction of the examinee's eye based on a change in the position information.

For example, the anterior segment acquisitor may be configured to acquire a first anterior segment image as the anterior segment image of at least one of the examinee's right and left eyes in a case where both of the examinee's right and left eyes are in the uncovered state and to acquire a second anterior segment image as the anterior segment image of at least one of the examinee's right and left eyes in a case where the other eye is in the covered state. In this case, the acquisitor may acquire the position information by analyzing the first anterior segment image and the second anterior segment image.

For example, the acquisitor may be configured to detect, for analyzing the anterior segment image, each portion (e.g., a black portion of the eye, an iris portion, a pupil portion, and a sclera portion (a white portion of the eye) of the examinee's eye. Moreover, the acquisitor may project, for analyzing the anterior segment image, the target onto the cornea of the examinee's eye to detect a target image formed on the cornea of the examinee's eye, for example. Needless to say, the acquisitor may be configured to detect, for analyzing the anterior segment image, a portion different from each portion of the examinee's eye and the target image.

For example, the acquisitor may be configured to perform edge detection to detect each portion of the examinee's eye or the target image. In this case, the acquisitor may be configured to detect rising and falling of luminance for edge detection, for example. Needless to say, the acquisitor may be configured so that each portion of the examinee's eye or the target image can be detected by image processing.

For example, the acquisitor may detect each portion of the examinee's eye or the target image by analysis processing to acquire the position information on the examinee's eye based on a detection result. For example, the acquisitor may be configured to acquire the position information on the examinee's eye based on at least any of pupil information, corneal apex information, etc. Note that the position information on the examinee's eye is not limited to the above-described information. For example, the position information on the examinee's eye may be information allowing acquisition of the visual line position (the visual axial position) of the examinee's eye.

For example, in the case of using the pupil information upon acquisition of the position information on the examinee's eye, the acquisitor may detect the pupil positions of the examinee's right and left eyes by the analysis processing of the anterior segment image, thereby acquiring the position information based on the detected pupil positions. For example, the subjective optometry apparatus in the present embodiment may be configured to detect the pupil position of the examinee's eye, thereby acquiring the position information based on the detected pupil position. Thus, tilting information on the examinee's eye can be easily acquired with a simple configuration.

Moreover, in the case of using the corneal apex information upon acquisition of the position information on the examinee's eye, the acquisitor may detect, by the analysis processing of the anterior segment image, the target image projected onto the corneas of the examinee's right and left eyes, thereby detecting the corneal apex position, for example. Further, the acquisitor may acquire the position information based on the detected corneal apex position. Note that the acquisitor may be configured to detect the cornea position from the anterior segment image without use of the target image, thereby acquiring the corneal apex information. Needless to say, the position information may be information calculated based on the pupil position information and the corneal apex position information, for example.

For example, the acquisitor may detect at least any one of first position information as the position information on the examinee's right-eye corrective optical system obtained when the examinee's right-eye corrective optical system is position-adjusted to the right examinee's eye and second position information as the position information on the examinee's left-eye corrective optical system obtained when the examinee's left-eye corrective optical system is position-adjusted to the left examinee's eye, and may acquire the position information on the examinee's eye based on at least any of the detected first position information and the detected second position information. In this case, for example, the corrective optical system preferably has the right-left pair of the examinee's right-eye corrective optical system and the examinee's left-eye corrective optical system, and the examinee's right-eye corrective optical system and the examinee's left-eye corrective optical system can be position-adjusted to the examinee's right and left eyes, respectively. Note that the first position information and the second position information may be information allowing identification of the position of the corrective optical system, for example. In this case, the first position information and the second position information may be the position coordinates of the corrective optical system, for example. Alternatively, the first position information and the second position information may be the movement amount of the corrective optical system, for example.

For example, the first position information may be position information on at least one member in the examinee's right-eye corrective optical system, the position information being obtained when the optical axis of the examinee's right-eye corrective optical system and the visual axis of the examinee's right eye are position-adjusted to each other. For example, the second position information may be position information on at least one member in the examinee's left-eye corrective optical system, the position information being obtained when the optical axis of the examinee's left-eye corrective optical system and the visual axis of the examinee's left eye are position-adjusted to each other.

<Determiner>

For example, the determiner may be configured to compare the acquired position information and standard data to determine whether or not subjective measurement can be implemented in the binocular open state of the examinee's right and left eyes, thereby acquiring the determination information. For example, the standard data may be data as the criterion for implementation of subjective measurement in the binocular open state. For example, the standard data may be position coordinate data, anterior segment image data, etc. Needless to say, the standard data may be data which can be used as the criterion for determination on whether or not subjective measurement can be implemented in the binocular open state.

For example, the determiner may be configured to acquire a determination result as the determination information. For example, the subjective optometry apparatus acquires the determination result as the determination information. That is, the determiner acquires the determination result indicating whether or not favorable binocular vision can be performed by the examinee's eyes, for example. Thus, the examiner refers to the determination result so that the state of binocular vision of the examinee's eyes can be easily determined.

Moreover, the determiner may acquire guide information as the determination information, for example. The guide information is information for guiding the examiner to the measurement mode of either the covering mode for performing subjective examination for one of the examinee's right and left eyes with the other eye being covered or the binocular open mode for performing subjective examination for one eye in the binocular open state. For example, the subjective optometry apparatus may acquire the guide information as the determination information. The guide information is information for guiding the examiner to the measurement mode of either the covering mode for performing subjective examination for one of the examinee's right and left eyes with the other eye being covered or the binocular open mode for performing subjective examination for one eye in the binocular open state. Thus, the examiner refers to the guide information so that a proper measurement mode can be selected in accordance with the examinee's eye.

<Determination Information Output Unit>

For example, the determination information output unit may be configured to display the determination information on a display (e.g., a monitor 4). For example, the subjective optometry apparatus displays the determination information on the display. Thus, the examiner refers to the displayed determination information so that the state of the examinee's eye can be easily recognized.

Moreover, the determination information output unit may be configured to print out the determination information, for example. In this case, the determination information output unit is configured to output (transfer) the determination information to a printer etc. via wireless communication, a communication cable, etc., for example. Note that the printer may be, for example, provided at a main body of the subjective optometry apparatus 1, or may be separately provided as a (separate) member different from the apparatus. Moreover, the determination information output unit may be configured to transmit the determination information to various members (e.g., a measurer 7), for example. In this case, various members may perform various types of control based on the received determination information, for example.

EXAMPLE

A subjective optometry apparatus according to one example of the present disclosure will be described below. For example, the subjective optometry apparatus may include a subjective measurer. Moreover, the subjective optometry apparatus may include an objective measurer. Note that in the present example, a subjective optometry apparatus including both of a subjective measurer and an objective measurer will be described by way of example.

FIG. 1 illustrates an external view of a subjective optometry apparatus 1 of the present example. For example, the subjective optometry apparatus 1 includes a housing 2, a presentation window 3, a monitor 4, a chin rest 5, a base 6, and an anterior segment imaging optical system 100. For example, the housing 2 includes a right-eye measurer 7R and a left-eye measurer 7L (details will be described later). Note that in description below, the right-eye measurer 7R and the left-eye measurer 7L may be collectively referred to as a "measurer 7" when the right-eye measurer 7R and the left-eye measurer 7L are not distinguished from each other.

For example, the presentation window 3 is used for presenting a target to an examinee. For example, target light fluxes from the measurers 7 are each projected onto the examinee's right eye ER and the examinee's left eye EL (see FIG. 3) as examinee's eyes via the presentation window 3. Note that in description below, the examinee's right eye ER and the examinee's left eye EL may be collectively referred to as an examinee's eye E when the examinee's right eye ER and the examinee's left eye EL are not distinguished from each other.

For example, the monitor (a display) 4 is configured to display optical characteristics (optical characteristic results such as a spherical refractivity S, a cylindrical refractivity C, and an astigmatic axial angle A) of the examinee's eye E. For example, the monitor 4 is a touch panel. That is, in the present example, the monitor 4 functions as an operating unit configured to receive input from a user (an examiner). For example, a signal corresponding to an operation instruction input via the monitor 4 is output to a later-described controller 70. Note that the monitor 4 is not necessarily a touch panel type monitor, and the monitor 4 and the operating unit may be provided as separate members. For example, in this case, at least any of operating units such as a mouse, a joystick, and a keyboard may be used as the operating unit.

For example, the monitor 4 may be a display mounted to the housing 2, or a display connected to the housing 2. In the latter case, a display of a personal computer may be used as the monitor 4, for example. Alternatively, a plurality of displays may be, as the monitor 4, used in combination.

For example, the chin rest is used for maintaining a constant distance between the examinee's eye E and the subjective optometry apparatus 1. Note that in the present example, the chin rest 5 is used to maintain a constant distance between the examinee's eye E and the subjective optometry apparatus 1. However, the member configured to maintain a constant distance as described above is not limited to the chin rest 5. For example, in the present example, a forehead rest or a face rest may be used to maintain a constant distance between the examinee's eye E and the subjective optometry apparatus 1. For example, the chin rest 5 and the housing 2 are fixed to the base 6.

<Measurer>

For example, the measurers 7 include the left-eye measurer 7L and the right-eye measurer 7R. For example, in the present example, the left-eye measurer 7L and the right-eye measurer 7R include identical members. That is, the subjective optometry apparatus 1 in the present example has a right-left pair of subjective measurers and a right-left pair of objective measurers. Needless to say, the left-eye measurer 7L and the right-eye measurer 7R may be configured such that at least some of the members are different from each other.

Figure 2:
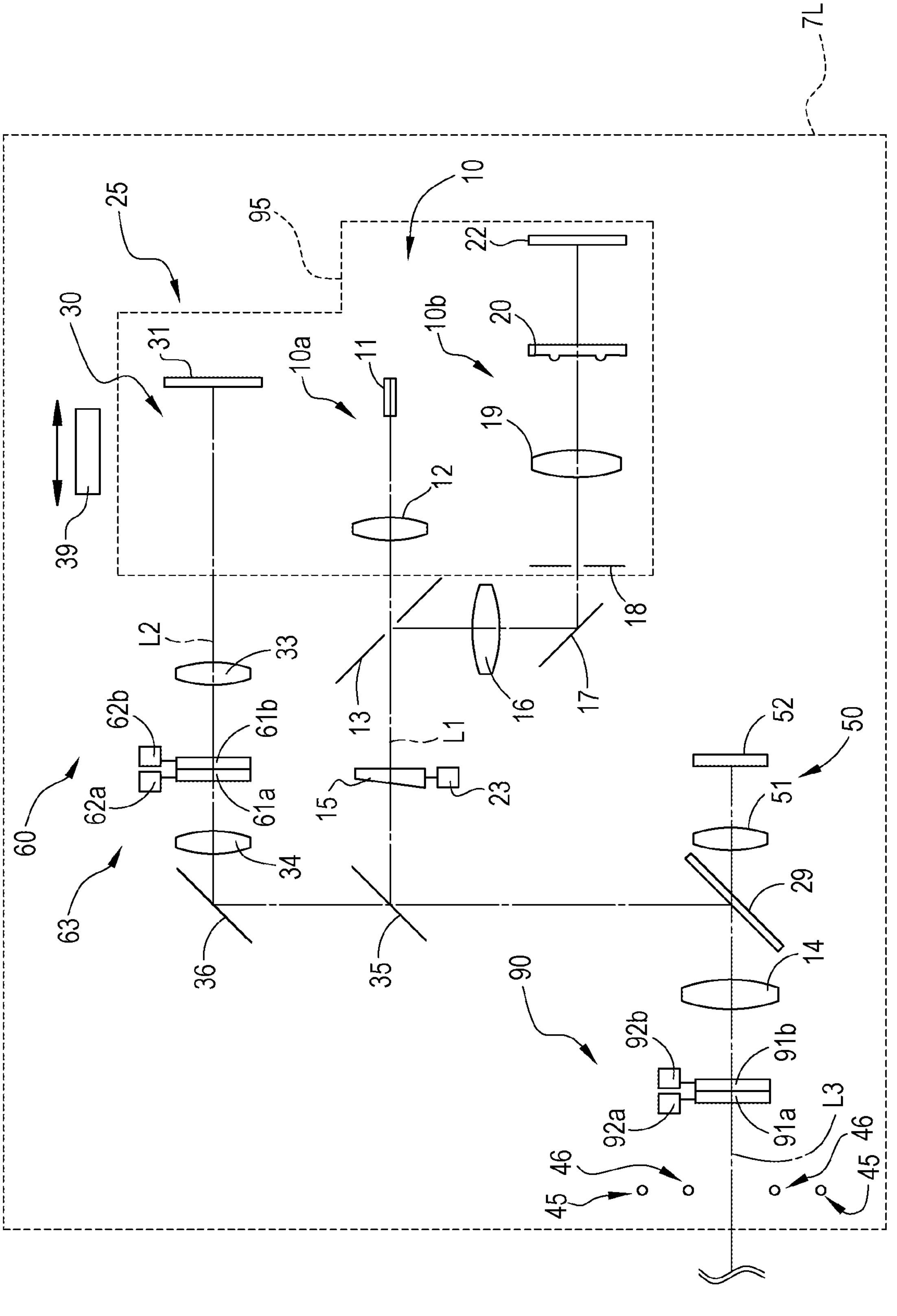
FIG. 2 is a drawing for describing a measurer configuration.

FIG. 2 is a drawing for describing the configuration of the measurer 7. In the present example, the left-eye measurer 7L will be described by way of example. Note that description of the right-eye measurer 7R is omitted because the right-eye measurer 7R has a configuration similar to that of the left-eye measurer 7L. For example, the left-eye measurer 7L includes a subjective measurement optical system 25, an objective measurement optical system 10, a first target projecting optical system 45, a second target projecting optical system 46, and an observing optical system 50.

<Subjective Measurement Optical System>

For example, the subjective measurement optical system 25 is used as a part of the configuration of a subjective measurer for subjectively measuring optical characteristics of the examinee's eye E (as will be described in detail later). The optical characteristics of the examinee's eye E may include the eye refractive power, contrast sensitivity, and binocular vision functions (such as the amount of phoria and stereoscopic function). In the present example, the subjective measurer for measuring the eye refractive power of the examinee's eye E will be described by way of example. The subjective measurement optical system 25 includes a light projecting optical system (target light projecting system) 30, a corrective optical system 60, and a correction optical system 90.

For example, the light projecting optical system 30 projects a target light flux toward the examinee's eye E. The light projecting optical system 30 is provided with, e.g., a display 31, a light projecting lens 33, a light projecting lens 34, a reflective mirror 36, a dichroic mirror 35, a dichroic mirror 29, and an objective lens 14. For example, the target light flux projected from the display 31 is projected toward the examinee's eye E via a plurality of optical members including the light projecting lens 33, the light projecting lens 34, the reflective mirror 36, the dichroic mirror 35, the dichroic mirror 29, and the objective lens 14 in that order.

On the display 31, there is displayed an examination target (as used during later-described subjective measurement, for example) such as a Landolt ring target or a fixation target (as used during later-described objective measurement, for example) for fixating the examinee's eye E, for example. For example, the target light flux from the display 31 is projected toward the examinee's eye E. For example, in the present example, a case where an LCD is used as the display 31 will be described below by way of example. Note that an organic electro luminescence (EL) display, a plasma display, etc. can be used as the display.

For example, the corrective optical system 60 is disposed on the optical path of the light projecting optical system 30. For example, the corrective optical system 60 is configured to change the optical characteristics of the target light flux. In the present example, an examinee's left-eye corrective optical system provided as the corrective optical system 60 in the left-eye measurer 7L will be described by way of example. Note that although description is omitted from the present example, the right-eye measurer 7R includes an examinee's right-eye corrective optical system. That is, the corrective optical system 60 has a right-left pair of the examinee's right-eye corrective optical system and the examinee's left-eye corrective optical system. Thus, position adjustment (alignment) of the examinee's left eye EL and position adjustment of the examinee's right eye ER can be separately performed. For example, the optical axis L2 of the examinee's left-eye corrective optical system and the visual axis of the examinee's left eye EL can be brought into coincident with each other by such position adjustment. Moreover, the optical axis L2 of the examinee's right-eye corrective optical system and the visual axis of the examinee's right eye ER can be brought into coincident with each other.

For example, the corrective optical system 60 includes an astigmatism corrective optical system 63 and a drive mechanism 39. For example, the astigmatism corrective optical system 63 is disposed between the light projecting lens 34 and the light projecting lens 33. For example, the astigmatism corrective optical system 63 is used to correct the target light flux in accordance with the cylindrical diopter power, the cylindrical axis (the astigmatic axis), etc. of the examinee's eye E. For example, the astigmatism corrective optical system 63 includes two positive cylindrical lenses 61*a* and 61*b* having mutually equal focal distances. The cylindrical lens 61*a* and the cylindrical lens 61*b* are independently rotated about the optical axis L2 by driving of rotating mechanisms 62*a* and 62*b*, respectively. Note that the present example describes the astigmatism corrective optical system 63 including the two positive cylindrical lenses 61*a* and 61*b*. However, the astigmatism corrective optical system 63 is not limited to above. The astigmatism corrective optical system 63 may be only configured so that the target light flux can be corrected in accordance with the cylindrical diopter power, the astigmatic axis, etc. of the examinee's eye E. In this case, the astigmatism corrective optical system 63 may be configured to move a corrective lens into and out of the optical path of the light projecting optical system 30.

For example, the drive mechanism 39 includes a motor and a slide mechanism. For example, the display 31 is integrally moved in the direction of the optical axis L2 by the drive mechanism 39. For example, during subjective measurement, the display 31 is moved such that the target presentation position (the presenting distance) with respect to the examinee's eye E is optically changed. In this way, the target light flux is corrected in accordance with the spherical refractive power (the spherical power) of the examinee's eye E. That is, the spherical power corrective optical system includes the movable display 31. Note that the spherical power corrective optical system is not limited to the above-described configuration. For example, the spherical power corrective optical system may have a number of optical elements, and may be configured to correct the target light flux by the optical elements disposed on the optical path. Moreover, the spherical power corrective optical system may also be configured to move a lens disposed on the optical path in the optical axis direction, for example.

Note that the present example describes, by way of example, the corrective optical system configured to correct the target light flux in accordance with the spherical power, the cylindrical diopter power, and the cylindrical axis of the examinee's eye E. However, the corrective optical system is not limited to above. For example, the corrective optical system configured to correct the target light flux in accordance with the prism value of the examinee's eye E may be provided. By providing the corrective optical system configured to correct the target light flux in accordance with the prism value, the target light flux can be corrected such that the target light flux is projected onto the examinee's eye E even in a case where the examinee's eye E is an eye with heterophoria.

Note that the present example has described, by way of example, the configuration in which the astigmatism corrective optical system 63 configured to correct the target light flux in accordance with the cylindrical diopter power and the cylindrical axis (the astigmatic axis) of the examinee's eye E and the corrective optical system (e.g., the drive mechanism 39) configured to correct the target light flux in accordance with the spherical power of the examinee's eye E are separately provided. However, the present disclosure is not limited to above, and there may be provided a corrective optical system configured to correct the target light flux in accordance with the spherical power, the cylindrical diopter power, and the astigmatic axis of the examinee's eye E, for example. That is, the corrective optical system in the present example may be an optical system configured to modulate wavefront. Alternatively, the corrective optical system may be an optical system configured to correct the target light flux in accordance with the spherical power, the cylindrical diopter power, the astigmatic axis, etc. of the examinee's eye E, for example. In this case, the corrective optical system may include a lens disc including a number of optical elements (e.g., a spherical lens, a cylindrical lens, and a dispersing prism) disposed on the same circumference, for example. In this case, as the lens disc is rotatably controlled by a driver (e.g., an actuator), an optical element (e.g., a cylindrical lens, a cross cylinder lens, or a rotary prism) desired by the examiner is disposed on the optical axis L2 with a rotation angle desired by the examiner. For example, switching etc. of the optical elements disposed on the optical axis L2 may be performed in such a manner that the examiner operates the operating unit such as the monitor 4.

Either one or a plurality of lens discs may be used. When a plurality of lens discs is disposed, a driver corresponding to each of the lens discs may be provided. For example, each lens disc is provided with an opening (or a OD lens) and a plurality of optical elements, forming a lens disc group. Representative types of the lens discs are a spherical lens disc including a plurality of spherical lenses with different powers; a cylindrical lens disc including a plurality of cylindrical lenses with different powers; and an auxiliary lens disc including a plurality of types of auxiliary lenses. In the auxiliary lens disc, at least a red filter/green filter, a prism, a cross cylinder lens, a polarization plate, a Maddox lens, or an auto cross cylinder lens is disposed. The cylindrical lenses are disposed so as to be rotatable by the driver about the optical axis L2. The rotary prism and the cross cylinder lens may be disposed so as to be rotatable by the driver about the respective optical axes.

Figure 3:
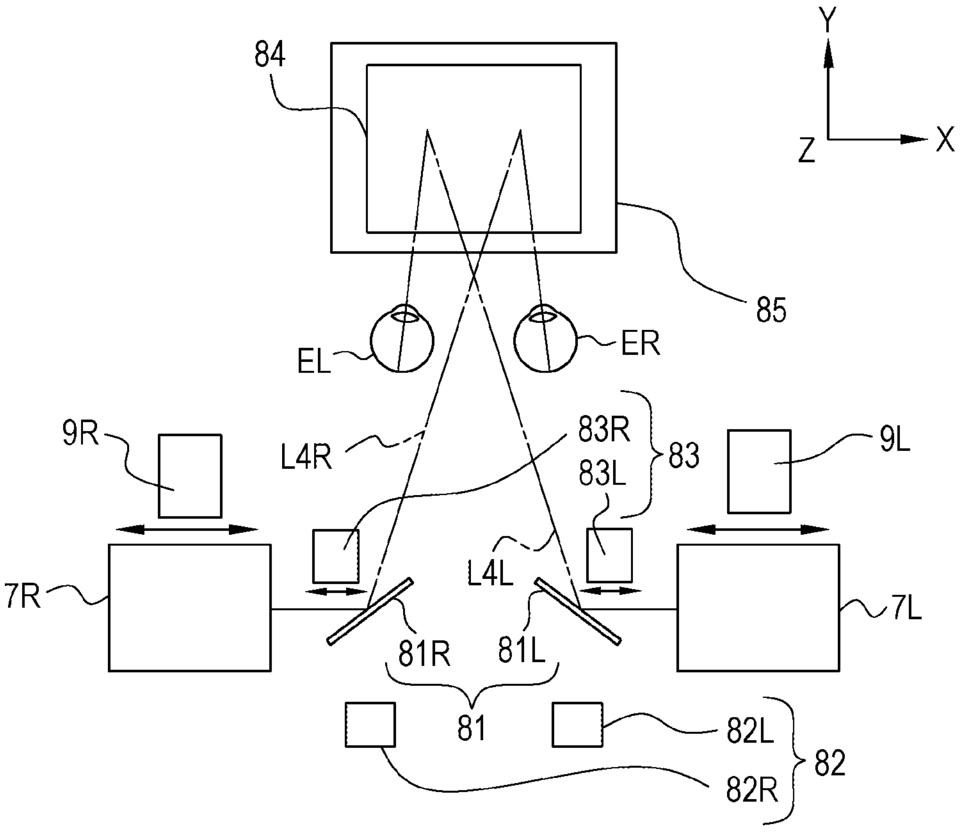
FIG. 3 is a schematic configuration diagram of the inside of the subjective optometry apparatus from the front.

For example, the correction optical system 90 is disposed between the objective lens 14 and a later-described deflecting mirror 81 (see FIG. 3). For example, the correction optical system 90 is used to correct optical aberration (e.g., astigmatism) caused in subjective measurement. For example, the correction optical system 90 includes two positive cylindrical lenses 91*a* and 91*b* having an equal focal distance. For example, the correction optical system 90 corrects the astigmatism by adjusting the cylindrical diopter power and the astigmatic axis. The cylindrical lens 91*a* and the cylindrical lens 91*b* are each independently rotated about an optical axis L3 by driving of rotating mechanisms 92*a* and 92*b*, respectively. Note that in the present example, the correction optical system 90 includes, by way of example, the two positive cylindrical lenses 91*a* and 91*b*, by way of example. However, the present disclosure is not limited to above, and the correction optical system 90 may be only configured so that the astigmatism can be corrected. In this case, the correction optical system 90 may be configured to move a correction lens into and out of the optical axis L3, for example.

Note that in the present example, the correction optical system 90 is, by way of example, disposed as a separate member from the corrective optical system 60. However, the present disclosure is not limited to above, and the corrective optical system 60 may also serve as the correction optical system 90, for example. In this case, the cylindrical diopter power and the cylindrical axis (the astigmatic axis) of the examinee's eye E is corrected in accordance with the amount of astigmatism. That is, the corrective optical system 60 is driven to correct the target light flux in accordance with the cylindrical diopter power and the astigmatic axis of the examinee's eye E in light of (while correcting) the amount of astigmatism. For example, since the corrective optical system 60 also serves as the correction optical system 90, complicated control is not necessary. Accordingly, the optical aberration can be corrected with a simple configuration. Moreover, since the corrective optical system 60 also serves as the correction optical system 90, it is not necessary to separately provide a corrective optical system for the optical aberration, for example. Accordingly, the optical aberration can be corrected with a simple configuration.

<Objective Measurement Optical System>

For example, the objective measurement optical system 10 is used as part of the configuration of the objective measurer configured to objectively measure the optical characteristics of the examinee's eye (details will be described later). Examples of the optical characteristics of the examinee's eye include eye refractive power, an ocular axial length, and a corneal shape. In the present example, the objective measurer configured to measure the eye refractive power of the examinee's eye will be described by way of example. For example, the objective measurement optical system 10 includes a projecting optical system 10*a*, a light receiving optical system 10*b*, and a correction optical system 90.

For example, the projecting optical system (a light projecting optical system) 10*a* projects a spot-shaped measurement target onto the fundus of the examinee's eye E via a pupil center portion of the examinee's eye E. For example, the light receiving optical system 10*b* extracts fundus reflected light in the form of a ring-shaped fundus reflection image via a pupil peripheral portion, the fundus reflected light being obtained by optical reflection by the fundus. The light receiving optical system 10*b* causes a two-dimensional imaging device 22 to capture the ring-shaped fundus reflection image.

For example, the projecting optical system 10*a* includes, on the optical axis L1 of the objective measurement optical system 10, a measurement light source (a light source) 11, a relay lens 12, a hole mirror 13, a prism 15, a driver (a motor) 23, a dichroic mirror 35, a dichroic mirror 29, and an objective lens 14. For example, the prism 15 is a light flux deflecting member. For example, the driver 23 is configured to rotatably drive the prism 15 about the optical axis L1. For example, the light source 11 is in a conjugate relation with the fundus of the examinee's eye E. Moreover, a hole portion of the hole mirror 13 is in a conjugate relation with the pupil of the examinee's eye E. For example, the prism 15 is disposed at a position away from a position conjugate with the pupil of the examinee's eye E. For example, the prism 15 causes the light flux passing therethrough to be eccentric with respect to the optical axis L1. Note that instead of the prism 15, a parallel flat plate as the light flux deflecting member may be disposed diagonally on the optical axis L1.

For example, the dichroic mirror 35 commonalizes the optical path of the subjective measurement optical system 25 and the optical path of the objective measurement optical system 10. That is, the dichroic mirror 35 causes the optical axis L2 of the subjective measurement optical system 25 and the optical axis L1 of the objective measurement optical system 10 to be coaxial with each other, for example. For example, the dichroic mirror 29 as an optical path dividing member reflects a light flux from the subjective measurement optical system 25 and measurement light from the projecting optical system 10*a*, and then, guides the light flux and the measurement light to the examinee's eye E.

For example, the light receiving optical system 10*b* and the projecting optical system 10*a* share the objective lens 14, the dichroic mirror 29, the dichroic mirror 35, the prism 15, and the hole mirror 13 of the projecting optical system 10*a*. The light receiving optical system 10*b* includes a relay lens 16 and a mirror 17, which are disposed on the optical path in the reflecting direction of the hole mirror 13; and a light receiving aperture 18, a collimator lens 19, a ring lens 20, and the two-dimensional imaging device 22, such as a CCD, which are disposed on the optical path in the reflecting direction of the mirror 17. For example, the light receiving aperture 18 and the two-dimensional imaging device 22 are in a conjugate relation with the fundus of the examinee's eye E. For example, the ring lens 20 includes a ring-shaped lens portion and a light shielding portion. The light shielding portion is a region other than the lens portion. The light shielding portion is provided with a light shielding coating. The ring lens 20 is in an optically conjugate positional relationship with the pupil of the examinee's eye E. For example, an output signal from the two-dimensional imaging device 22 is received by the controller 70.

For example, the dichroic mirror 29 reflects reflected light (fundus reflected light) toward the light receiving optical system 10*b*, the reflected light being obtained as the measurement light from the projecting optical system 10*a* is reflected by the fundus of the examinee's eye E. For example, the dichroic mirror 29 also transmits anterior segment observation light and alignment light, and guides such light to the observing optical system 50. For example, the dichroic mirror 35 reflects the above-described fundus reflected light toward the light receiving optical system 10*b*.

Note that the configuration of the objective measurement optical system 10 is not limited to the above-described configuration. The objective measurement optical system 10 may have other known configurations. For example, the objective measurement optical system 10 may be configured to project a ring-shaped measurement target from the pupil peripheral portion onto the fundus. In this case, in the objective measurement optical system 10, ring-shaped fundus reflected light extracted from the pupil center portion may be received by the two-dimensional imaging device 22.

Note that the configuration of the objective measurement optical system 10 is not limited to the above-described configuration. The objective measurement optical system 10 may be a measurement optical system having a light projecting optical system and a light receiving optical system. The light projecting optical system projects the measurement light toward the fundus of the examinee's eye E. The light receiving optical system receives, using a photo detector, reflected light acquired through reflection of the measurement light by the fundus. For example, an eye refractive power measurement optical system may include a Shack-Hartmann sensor. Needless to say, apparatuses (e.g., a phase difference type apparatus configured to project a slit) employing other measurement methods may be utilized.

Note that the configuration of the objective measurement optical system 10 is not limited to the above-described configuration. The objective measurement optical system 10 may have other known configurations. For example, the objective measurement optical system 10 may be configured to project a ring-shaped measurement target from the pupil peripheral portion onto the fundus. In this case, in the objective measurement optical system 10, ring-shaped fundus reflected light extracted from the pupil center portion may be received by the two-dimensional imaging device 22.

For example, the light source 11 of the projecting optical system 10*a* and the light receiving aperture 18, the collimator lens 19, the ring lens 20, and the two-dimensional imaging device 22 of the light receiving optical system 10*b* are integrally movable in the optical axis direction. In the present example, the light source 11 of the projecting optical system 10*a* and the light receiving aperture 18, the collimator lens 19, the ring lens 20, and the two-dimensional imaging device 22 of the light receiving optical system 10*b* are, for example, integrally moved in the direction of the optical axis L1 by the drive mechanism 39 configured to drive the display 31. That is, the display 31, the light source 11 of the projecting optical system 10*a*, and the light receiving aperture 18, the collimator lens 19, the ring lens 20, and the two-dimensional imaging device 22 of the light receiving optical system 10*b* are synchronized and integrally moved as a drive unit 95. Needless to say, these members may be configured such that each member is separately driven.

For example, the drive unit 95 moves part of the objective measurement optical system 10 in the optical axis direction such that an outer light flux ring enters the two-dimensional imaging device 22 with respect to each meridian direction. That is, part of the objective measurement optical system 10 is moved in the optical axis L1 direction in accordance with the spherical refractive error (the spherical refractive power) of the examinee's eye E, and in this way, the spherical refractive error is corrected. In addition, the light source 11, the light receiving aperture 18, and the two-dimensional imaging device 22 thereby become optically conjugate with the fundus of the examinee's eye E. A position to which the drive mechanism 39 has been moved is detected by a not-shown potentiometer. Note that the hole mirror 13 and the ring lens 20 are disposed conjugate with the pupil of the examinee's eye E at a certain magnification ratio regardless of the amount of movement of the drive unit 95.

In the above-described configuration, the measurement light flux emitted from the light source 11 forms a spot-shaped point light source image on the fundus of the examinee's eye E by way of the relay lens 12, the hole mirror 13, the prism 15, the dichroic mirror 35, the dichroic mirror 29, and the objective lens 14. In this case, by the prism 15 rotating about the optical axis, the pupil-projected image (the light flux projected onto the pupil) of the hole portion of the hole mirror 13 is eccentrically rotated at high speed. The point light source image projected onto the fundus is reflected and scattered, exits the examinee's eye E, and is then condensed by the objective lens 14. Thereafter, such light is again condensed at the position of the light receiving aperture 18 through the dichroic mirror 29, the dichroic mirror 35, the prism 15 rotating at high speed, the hole mirror 13, the relay lens 16, and the mirror 17. As the condensed light passes through the collimator lens 19 and the ring lens 20, a ring-shaped image is formed on the two-dimensional imaging device 22.

The prism 15 is disposed on the common optical path of the projecting optical system 10*a* and the light receiving optical system 10*b*. Accordingly, the reflected light flux from the fundus passes through the same prism 15 as the prism through which the light flux of the projecting optical system 10*a* passes. Accordingly, in the optical system subsequent to the prism 15, an inverted scan is implemented as if there were no eccentricity between the projected light flux and the reflected light flux (received light flux) on the pupil.

The objective measurement optical system 10 shares the correction optical system 90 with the subjective measurement optical system 25. Of course, a separate correction optical system may be provided for the objective measurement optical system 10.

<First Target Projecting Optical System and Second Target Projecting Optical System>

In the present example, the first target projecting optical system 45 and the second target projecting optical system 46 are disposed between the correction optical system 90 and the deflecting mirror 81. Needless to say, the arrangement positions of the first target projecting optical system 45 and the second target projecting optical system 46 are not limited to above. For example, the first target projecting optical system 45 and the second target projecting optical system 46 may be provided at a cover of the housing 2. In this case, the first target projecting optical system 45 and the second target projecting optical system 46 may be disposed at the periphery of the presentation window 3, for example.

In the first target projecting optical system 45, a plurality of infrared light sources is disposed concentrically at 45° intervals about the optical axis L3. The plurality of infrared light sources is disposed bilaterally symmetric across a vertical plane passing the optical axis L3. The first target projecting optical system 45 emits near-infrared light for projecting an alignment target onto the cornea of the examinee's eye E. The second target projecting optical system 46 includes six infrared light sources disposed at different positions from those of the first target projecting optical system 45. In this case, the first target projecting optical system 45 is configured to project a target at infinity onto the cornea of the examinee's eye E from the right-left direction. The second target projecting optical system 46 is configured to project a target at a finite distance onto the cornea of the examinee's eye E from the up-down direction or an oblique direction. Note that for the sake of convenience of description, FIG. 2 only illustrates part of the first target projecting optical system 45 and part of the second target projecting optical system 46. Note that the second target projecting optical system 46 is also used as an anterior segment illumination configured to illuminate the anterior segment of the examinee's eye E. The second target projecting optical system 46 may also be utilized as a target for corneal shape measurement. Further, the light source for the first target projecting optical system 45 and the light source for the second target projecting optical system 46 are not limited to point light sources. These light sources may be ring-shaped light sources or linear light sources, for example.

<Observing Optical System>

The observing optical system (imaging optical system) 50 shares the objective lens 14 and the dichroic mirror 29 with the subjective measurement optical system 25 and the objective measurement optical system 10. In addition, the observing optical system 50 is provided with an imaging lens 51 and the two-dimensional imaging device 52. The two-dimensional imaging device 52 has an imaging surface disposed, e.g., at a substantially conjugate position with respect to the anterior segment of the examinee's eye E. For example, an output signal from the two-dimensional imaging device 52 is received by the controller 70. In this way, an image of the anterior segment of the examinee's eye E is captured by the two-dimensional imaging device 52 and displayed on the monitor 4. The observing optical system 50 also serves as an optical system for detecting an alignment target image formed by the first target projecting optical system 45 and the second target projecting optical system 46 on the cornea of the examinee's eye E. The position of the alignment target image is detected by the controller 70.

<Internal Configuration of Subjective Optometry Apparatus>

Figure 4:
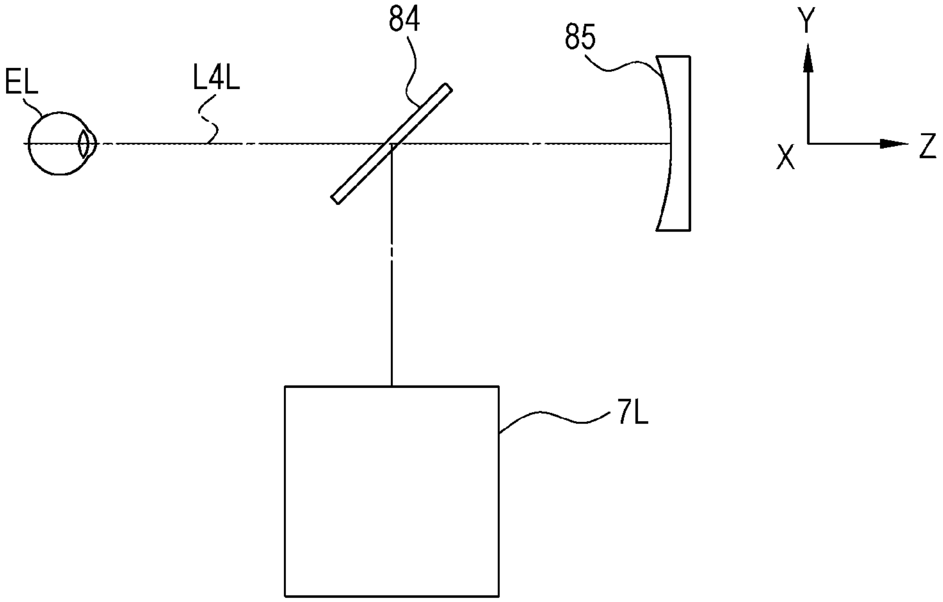
FIG. 4 is a schematic configuration diagram of the inside of the subjective optometry apparatus from the side.
Figure 5:
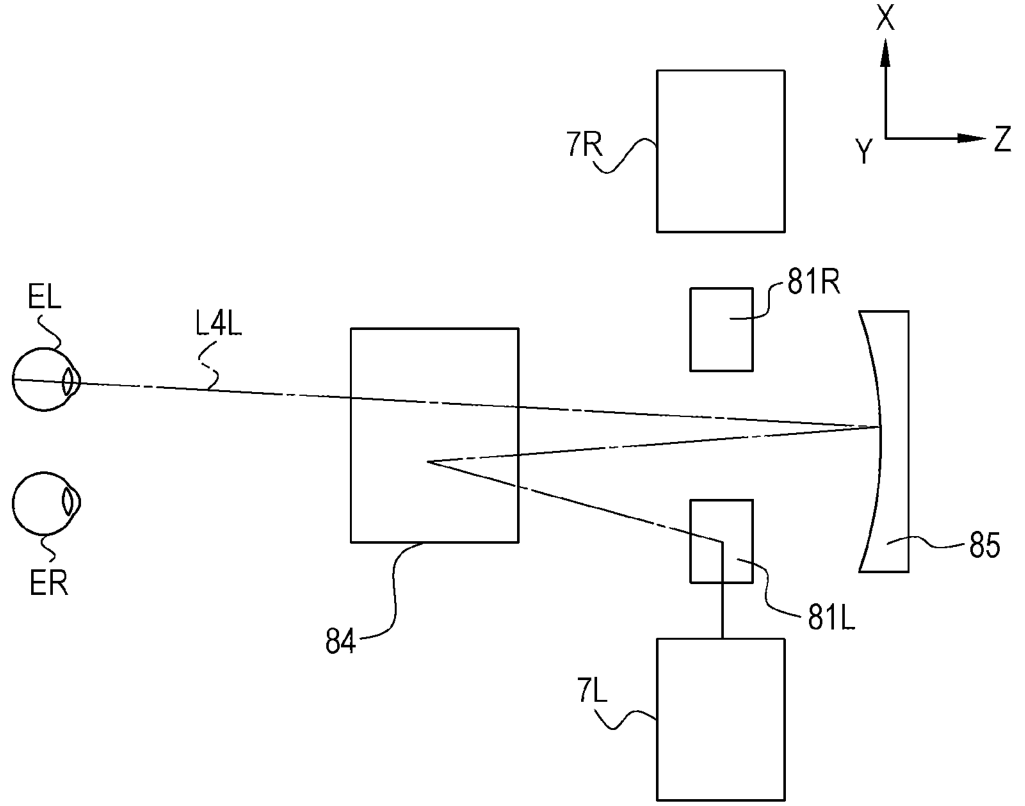
FIG. 5 is a schematic configuration diagram of the inside of the subjective optometry apparatus from above.

The internal configuration of the subjective optometry apparatus 1 will be described. FIG. 3 is a schematic configuration diagram of the interior of the subjective optometry apparatus 1 according to the present example, as viewed from the front (from direction A in FIG. 1). FIG. 4 is a schematic configuration diagram of the interior of the subjective optometry apparatus 1 according to the present example, as viewed from the side (from direction B in FIG. 1). FIG. 5 is a schematic configuration diagram of the interior of the subjective optometry apparatus 1 according to the present example, as viewed from the top (from direction C in FIG. 1). In FIG. 3, for convenience of description, the optical axis of the reflected light by the half mirror 84 is omitted. In FIG. 4, for convenience of description, the optical axis of the left-eye measurer 7L is illustrated whereas the optical axis of the right-eye measurer 7R is omitted. In FIG. 5, the optical axis of the left-eye measurer 7L is illustrated whereas the optical axis of the right-eye measurer 7R is omitted for convenience of description.

The subjective optometry apparatus 1 is provided with the subjective measurer and the objective measurer, for example. The subjective measurer is provided with the measurer 7, the deflecting mirror 81, a driver 82, a driver 83, a half mirror 84, and a concave mirror 85. Of course, the configuration of the subjective measurer is not limited to such configuration. For example, the objective measurer is provided with the measurer 7, the deflecting mirror 81, the half mirror 84, and the concave mirror 85. Of course, the configuration of the objective measurer is not limited to such configuration.

For example, the subjective optometry apparatus 1 has a left-eye driver 9L and a right-eye driver 9R. The left-eye driver 9L and the right-eye driver 9R are respectively capable of moving the left-eye measurer 7L and the right-eye measurer 7R in the X-direction. For example, by moving the left-eye measurer 7L and the right-eye measurer 7R, a distance between the deflecting mirror 81 and the measurer 7 is changed. As a result, the presentation position of the target light flux in the Z-direction is changed. In this way, the target light flux corrected by the corrective optical system 60 can be guided to the examinee's eye E. That is, the position of the measurer 7 in the Z-direction can be adjusted such that the image of the target light flux corrected by the corrective optical system 60 is formed at the fundus of the examinee's eye E.

For example, the deflecting mirror 81 has a pair of a right-eye deflecting mirror 81R and a left-eye deflecting mirror 81L that are respectively disposed on the right and left. For example, the deflecting mirror 81 is disposed between the corrective optical system 60 and the examinee's eye E. That is, the corrective optical system 60 has a right-left pair of a right-eye corrective optical system and a left-eye corrective optical system. The left-eye deflecting mirror 81L is disposed between the left-eye corrective optical system and the examinee's left eye EL. The right-eye deflecting mirror 81R is disposed between the right-eye corrective optical system and the examinee's right eye ER. Preferably, the deflecting mirror 81 is disposed at a position conjugate with the pupil, for example.

For example, the left-eye deflecting mirror 81L reflects the light flux projected from the left-eye measurer 7L, and guides the light flux to the examinee's left eye EL. For example, the left-eye deflecting mirror 81L also reflects reflected light obtained by optical reflection by the examinee's left eye EL, and guides the reflected light to the left-eye measurer 7L. For example, the right-eye deflecting mirror 81R reflects the light flux projected from the right-eye measurer 7R, and guides the light flux to the examinee's right eye ER. For example, the right-eye deflecting mirror 81R also reflects reflected light obtained by optical reflection by the examinee's right eye ER, and guides the reflected light to the right-eye measurer 7R. Note that in the present example, the deflecting mirror 81 is described as one example of the deflecting member configured to reflect the light flux projected from the measurer 7 and guide the light flux to the examinee's eye E. However, the deflecting member is not limited to above. The deflecting member may be any member configured to reflect the light flux projected from the measurer 7 and guide the light flux to the examinee's eye E. Examples of other deflecting members include a prism and a lens.

The driver 83 is provided with a motor (driver) and the like, for example. The driver 83 includes, e.g., a driver 83R for driving the right-eye deflecting mirror 81R, and a driver 83L for driving the left-eye deflecting mirror 81L. Through the driving of the driver 83, the deflecting mirror 81 can be moved in the X-direction, for example. As the right-eye deflecting mirror 81R and the left-eye deflecting mirror 81L are moved, for example, the distance between the right-eye deflecting mirror 81R and the left-eye deflecting mirror 81L is modified. In this way, the distance between the right-eye optical path and the left-eye optical path in the X-direction can be modified in accordance with the interpupillary distance of the examinee's eyes E.

The driver 82 is provided with a motor (driver) and the like, for example. The driver 82 includes, by way of example, a driver 82R for driving the right-eye deflecting mirror 81R, and a driver 82L for driving the left-eye deflecting mirror 81L. The driver 82 is driven, e.g., to move the deflecting mirror 81 rotationally. For example, the driver 82 causes the deflecting mirror 81 to rotate with respect to a rotational axis in the horizontal direction (the X-direction) and a rotational axis in the vertical direction (Y-direction). That is, the driver 82 causes the deflecting mirror 81 to rotate in the X- and Y-directions. The rotating direction of the deflecting mirror 81 may be either the horizontal direction or the vertical direction.

The concave mirror 85 is shared by the right-eye measurer 7R and the left-eye measurer 7L, for example. For example, the concave mirror 85 is shared by a right-eye optical path including the right-eye corrective optical system, and a left-eye optical path including the left-eye corrective optical system. Specifically, the concave mirror 85 is disposed at a position passing both the right-eye optical path including the right-eye corrective optical system, and the left-eye optical path including the left-eye corrective optical system. Of course, the concave mirror 85 may not be configured to be shared by the optical paths. That is, a concave mirror may be provided for each of the right-eye optical path including the right-eye corrective optical system, and the left-eye optical path including the left-eye corrective optical system. The concave mirror 85 guides the target light flux that has passed through the corrective optical system to the examinee's eye E, and forms an image of the target light flux, having passed through the corrective optical system, in front of the examinee's eye E, for example. In the present example, the configuration includes the use of the concave mirror 85. However, this is merely by way of example and, instead of the concave mirror 85, various optical members may be used. For example, a lens or a planar mirror may be used as the optical member.

The concave mirror 85 is used commonly for the subjective measurer and the objective measurer, for example. For example, the target light flux projected from the subjective measurement optical system 25 is projected onto the examinee's eye E via the concave mirror 85. In addition, for example, the measurement light projected from the objective measurement optical system 10 is projected onto the examinee's eye E via the concave mirror 85. In addition, for example, the reflected light of the measurement light projected from the objective measurement optical system 10 is guided to the light receiving optical system 10*b* of the objective measurement optical system 10 via the concave mirror 85. In the present example, the reflected light of the measurement light projected from the objective measurement optical system 10 is guided to the light receiving optical system 10*b* of the objective measurement optical system 10 via the concave mirror 85. However, this is merely by way of example, and the reflected light of the measurement light projected from the objective measurement optical system 10 may be guided to the light receiving optical system 10*b* of the objective measurement optical system 10 not via the concave mirror 85.

More specifically, in the present example, at least the optical axis between the concave mirror 85 and the examinee's eye E in the subjective measurer and the optical axis between the concave mirror 85 and the examinee's eye E in the objective measurer are coaxial, for example. For example, in the present example, the optical axis L2 of the subjective measurement optical system 25 and the optical axis L1 of the objective measurement optical system 10 are combined by the dichroic mirror 35. Accordingly, the optical axis L2 and the optical axis L1 are coaxial.

<Optical Path of Subjective Measurer>

In the following, the optical path of the subjective measurer will be described. For example, the subjective measurer reflects the target light flux that has passed through the corrective optical system 60 toward the examinee's eye E, using the concave mirror 85, thereby guiding the target light flux to the examinee's eye. The subjective measurer forms an image of the target light flux, having passed through the corrective optical system 60, in front of the examinee's eye E so that the distance sensed by the examinee to exist between the formation position of the image and the examinee's eye E becomes an optically predetermined examination distance. That is, the concave mirror 85 reflects the target light flux so as to become substantially parallel light fluxes. Accordingly, for the examinee, it appears as if the target image is located farther than the actual distance between the examinee's eye E and the display 31. That is, the use of the concave mirror 85 enables the target image to be presented to the examinee as if the image of the target light flux (target image) were located at a position corresponding to the predetermined examination distance.

The optical path of the subjective measurer will be described in greater detail. In the following description, the left-eye optical path will be described by way of example. The right-eye optical path has a similar configuration to the left-eye optical path. For example, in the left-eye subjective measurer, the target light flux projected from the display 32 of the left-eye measurer 7L enters the astigmatism corrective optical system 63 via the light projecting lens 33. The target light flux that has passed through the astigmatism corrective optical system 63 enters the correction optical system 90 via the reflective mirror 36, the dichroic mirror 35, the dichroic mirror 29, and the objective lens 14. The target light flux that has passed through the correction optical system 90 is emitted from the left-eye measurer 7L, and projected onto the left-eye deflecting mirror 81L. The target light flux emitted from the left-eye measurer 7L and reflected by the left-eye deflecting mirror 81 is then reflected by the half mirror 84 toward the concave mirror 85. The target light flux reflected by the concave mirror passes through the half mirror 84 and reaches the examinee's left eye EL.

In this way, with reference to the eyeglass wearing position for the examinee's left eye EL (for example, approximately 12 mm from the corneal apex), the target image corrected by the corrective optical system 60 is formed on the fundus of the examinee's left eye EL. This is as if the astigmatism corrective optical system 63 were disposed in front of the eye, and as if the adjustment of the spherical power by the spherical power corrective optical system (in the present example, by the driving of the drive mechanism 39) were performed in front of the eye. Thus, the examinee can sight the target image in a natural state via the concave mirror 85. In the present example, the right-eye optical path has a similar configuration to the left-eye optical path. With reference to the eyeglass wearing positions (such as approximately 12 mm from the corneal apex) for both of the examinee's eyes ER and EL, the target images corrected by the right-left pair of corrective optical systems 60 are formed on the fundi of the examinee's eyes. In this way, the examinee responds to the examiner while directly gazing at the target in a natural visual state. The correction by the corrective optical system 60 is implemented until the examinee can properly see the examination target. Based on the corrective value, the optical characteristics of the examinee's eye are subjectively measured.

<Optical Path of Objective Measurer>

The optical path of the objective measurer will be described next. In the following description, the left-eye optical path will be described by way of example. The right-eye optical path has a similar configuration to the left-eye optical path. In the left-eye objective measurer, for example, the measurement light emitted from the light source 11 of the projecting optical system 10*a* in the objective measurement optical system 10 enters the correction optical system 90 via the relay lens 12 to the objective lens 14. The measurement light that has passed through the correction optical system 90 is emitted from the left-eye measurer 7L, and projected onto the left-eye deflecting mirror 81L. The measurement light emitted from the left-eye measurer 7L and reflected by the left-eye deflecting mirror 81 is reflected by the half mirror 84 toward the concave mirror 85. The measurement light reflected by the concave mirror passes through the half mirror 84 and reaches the examinee's left eye EL, forming a spot of point light source image on the fundus of the examinee's left eye EL. In this case, the pupil-projected image due to the hole portion of the hole mirror 13 (projected light flux on the pupil) is eccentrically rotated at high speed by the prism 15 rotated about the optical axis.

The light of the point light source image formed on the fundus of the examinee's left eye EL is reflected and scattered by the examinee's left eye EL and then exits the examinee's left eye EL. The light travels along the optical path that has been traveled by the measurement light, and is condensed by the objective lens 14. The condensed light passes through the dichroic mirror 29, the dichroic mirror 35, the prism 15, the hole mirror 13, and the relay lens 16, and is then reflected by the mirror 17. The reflected light from the mirror 17 is again condensed at the opening of the light receiving aperture 18. The condensed light is further made into substantially parallel light fluxes (in the case of emmetropic eye) by the collimator lens 19. The substantially parallel light fluxes are extracted by the ring lens 20 in the form of a ring-shaped light flux. The ring-shaped light flux is received by the imaging device 22 in the form of a ring image. By analyzing the received ring image, the optical characteristics of the examinee's eye E can be measured objectively.

<Anterior Segment Imaging Optical System>

For example, the anterior segment imaging optical system 100 (hereinafter referred to as an "imaging optical system 100") includes a not-shown imaging device and a not-shown lens. For example, the imaging optical system 100 is configured to acquire an anterior segment image of at least one of the examinee's right and left eyes. That is, the imaging optical system 100 is configured to image either of the examinee's left eye EL or the examinee's right eye ER, thereby acquiring the anterior segment image of such an eye. For example, capturing of the anterior segment image by the imaging optical system 100 is controlled by the later-described controller 70. Moreover, the anterior segment image captured by the imaging optical system 100 is analyzed by the later-described controller 70, for example.

<Controller>

Figure 6:
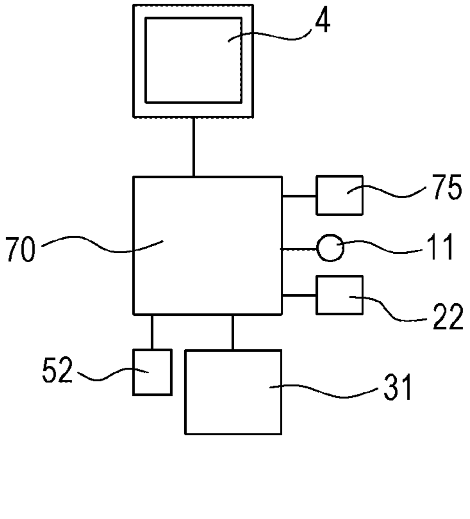
FIG. 6 illustrates a control system of the subjective optometry apparatus.

FIG. 6 illustrates a control system of the subjective optometry apparatus 1 of the present example. For example, various members such as the monitor 4, a non-volatile memory 75, and the light source 11, the imaging device 22, the display 31, and the two-dimensional imaging device 52 provided at the measurer 7 are electrically connected to the controller 70. Moreover, the drivers 9, the drive mechanism 39, the rotating mechanisms 62*a* and 62*b*, the driver 83, and not-shown drivers each provided at the rotating mechanisms 92*a* and 92*b* are electrically connected to the controller 70, for example.

For example, the controller 70 includes a CPU (a processor), a RAM, and a ROM. For example, the CPU is configured to control each member of the subjective optometry apparatus 1. For example, the RAM is configured to temporarily store various types of information. For example, in the ROM, various programs for controlling operation of the subjective optometry apparatus 1, target data for various examinations, and default values are stored. Note that the controller 70 may include a plurality of CPUs.

For example, the nonvolatile memory 75 (hereafter referred to as a "memory 75") is a non-transitory storage medium (recording medium) capable of retaining stored contents even when a power supply is cut off. Examples of the memory 75 include a hard disk drive, a flash ROM, and a USB memory detachably mounted to the subjective optometry apparatus 1. In the memory 75, a control program for controlling the subjective measurer and the objective measurer is stored, for example. This control program is, for example, a subjective optometry program to be executed by the CPU (the processor) of the subjective optometry apparatus 1 (the controller 70), thereby causing the subjective optometry apparatus 1 (the controller 70) to execute acquiring position information on at least one of the examinee's right and left eyes, determining, based on the position information, availability of binocular fusion by the examinee's right and left eyes to acquire determination information, and outputting the determination information.

<Control Operation>

Operation of the subjective optometry apparatus having the above-described configuration will be described. In a binocular open state close to natural vision, tightness and unnecessary adjustment are less caused at the examinee's eyes. It has been considered that in the binocular open state, proper subjective measurement is more easily performed as compared to a monocular covering state in which one eye is covered by means of a covering member (e.g., an occluder). However, in a case where the examinee's eye E is an eye with heterotropia, it is difficult for the examinee to correctly direct the visual lines of both eyes to the fixation target (in other words, binocular vision is difficult for the examinee's eyes E with heterotropia). For this reason, implementation of subjective measurement in the monocular covering state might be sometimes preferable for the examinee's eye E with heterotropia.

For example, determination on whether subjective measurement is implemented in the binocular open state or the monocular covering state is made by a cover test performed before the start of subjective measurement. In an examination method as the cover test, both eyes of the examinee are fixated to the fixation target (e.g., a target corresponding to the minimum visual acuity value). When an eye (an unmeasured eye) not targeted for measurement is covered, movement of an eye (a measurement target eye) targeted for measurement is identified. For example, in the cover test, heterotropia can be classified based on the visual line direction of the moved measurement target eye.

Figure 7A:
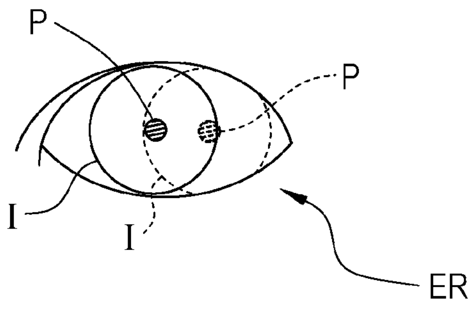
FIGS. 7A to 7D are drawings for describing heterotropia classifications.
Figure 7B:
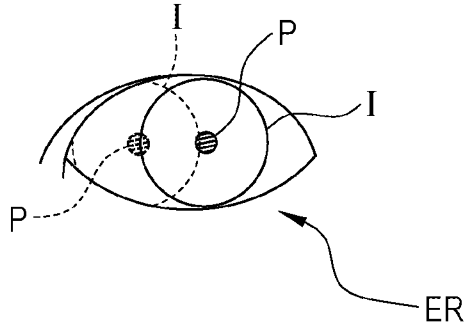
Figure 7C:
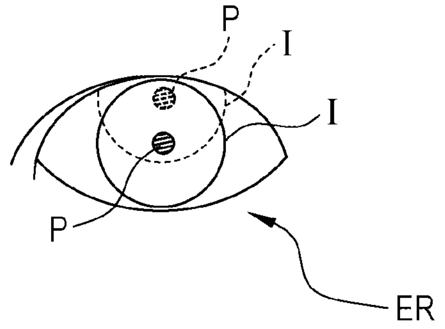
Figure 7D:
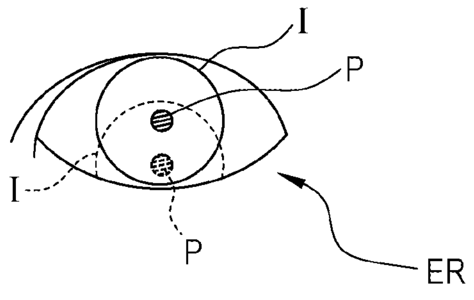

Classification of heterotropia by means of movement of the visual line direction of the measurement target eye will be described below. In the present example, the examinee's left eye EL is the unmeasured eye, and the examinee's right eye ER is the measurement target eye. FIGS. 7A to 7D illustrate heterotropia classifications. FIG. 7A illustrates esotropia. FIG. 7B illustrates exotropia. FIG. 7C illustrates hypertropia. FIG. 7D illustrates hypotropia. Moreover, in FIGS. 7A to 7D, an iris position I and a pupil position P before movement of the visual line direction are indicated by dashed lines, and the iris position I and the pupil position P after movement of the visual line direction are indicated by solid lines.

For example, when a state in which the fields of vision of the examinee's left eye EL and the examinee's right eye ER are open is brought into a state in which the examinee's left eye EL (the unmeasured eye) is covered, the examinee's right eye ER (the measurement target eye) moves outward as illustrated in FIG. 7A. Heterotropia is classified according to the moving direction of the visual line (the visual line direction) of one (e.g., the measurement target eye) of the examinee's right and left eyes with respect to the visual line (the visual line direction) of the other eye (e.g., the unmeasured eye). For example, in a case where the measurement target eye (the visual line of the measurement target eye) moves outward as illustrated in FIG. 7A when the unmeasured eye is covered, it is determined that the measurement target eye is esotropia. Similarly, in a case where the measurement target eye moves inward as illustrated in FIG. 7B when the unmeasured eye is covered, it is determined that the measurement target eye is exotropia, for example. Moreover, in a case where the measurement target eye moves downward as illustrated in FIG. 7C when the unmeasured eye is covered, it is determined that the measurement target eye is hypertropia, for example. Further, in a case where the measurement target eye moves upward as illustrated in FIG. 7D when the unmeasured eye is covered, it is determined that the measurement target eye is hypotropia, for example.

For example, the subjective optometry apparatus 1 in the present example is capable of performing control processing while replicating the above-described cover test. That is, the subjective optometry apparatus 1 in the present example can identify the measurement target eye in each of the binocular open state as a state in which the field of vision of the unmeasured eye is not covered and the monocular covering state as a state in which the field of vision of the unmeasured eye is covered, thereby determining movement of the visual line (the visual line direction) of the measurement target eye.

Note that a case where the measurement target eye is identified by the control processing performed while replicating the cover test will be described below by way of example. However, the present disclosure is not limited to above, and the visual line direction of the measurement target eye in a case where at least one of the examinee's right and left eyes is in an uncovered state may be identified in the present example, for example. Alternatively, in the present example, the visual line direction of the unmeasured eye in a case where at least one of the examinee's right and left eyes is in the uncovered state may be identified, for example. As another alternative, in the present example, both of the visual line direction of the measurement target eye and the visual line direction of the unmeasured eye in a case where at least one of the examinee's right and left eyes is in the uncovered state may be identified, for example. That is, at least one of the visual line direction of the examinee's right eye ER and the visual line direction of the examinee's left eye EL in the monocular covering state in which the examinee's left eye EL is covered, but the examinee's right eye ER is not covered may be identified, for example. As still another alternative, at least one of the visual line direction of the examinee's right eye ER and the visual line direction of the examinee's left eye EL in the monocular covering state in which the examinee's right eye ER is covered, but the examinee's left eye EL is not covered may be identified, for example.

As still another alternative, in the present example, the visual line direction of the measurement target eye in the binocular open state (the uncovered state) in which both of the examinee's right and left eyes are not covered may be identified, for example. As still another alternative, the visual line direction of the unmeasured eye in the binocular open state may be identified, for example. As still another alternative, in the present example, both of the visual line direction of the measurement target eye and the visual line direction of the unmeasured eye in the binocular open state may be identified, for example. That is, at least one of the visual line direction of the examinee's right eye ER and the visual line direction of the examinee's left eye EL in the binocular open state may be identified, for example.

For example, the controller 70 is capable of controlling the display state of the display 31 provided at the measurer 7 on an unmeasured eye side, thereby switching a measurement state between the binocular open state and the monocular covering state. For example, in the binocular open state, the controller 70 displays the fixation target and a background target on the displays 31 on a measurement target eye side and the unmeasured eye side. For example, in the monocular covering state, the controller 70 displays the fixation target and the background target on the display 31 on the measurement target eye side. On the other hand, the controller 70 displays the background target on the display 31 on the unmeasured eye side, but does not display the fixation target, for example. In this state, the controller 70 may turn off a main power supply of the display on the unmeasured eye side, thereby lighting off the display on the unmeasured eye side. Alternatively, the controller 70 may adjust a backlight of the display on the unmeasured eye side, thereby lighting off the display on the unmeasured eye side. As another alternative, the controller 70 may display a black background target on the display 31 on the unmeasured eye side, for example. For example, in the present example, the controller 70 is capable of switching the display state of the display 31 as described above, thereby bringing the monocular covering state. Note that the monocular covering state may be brought in such a manner that the covering member is disposed in front of the unmeasured eye.

Figure 8:
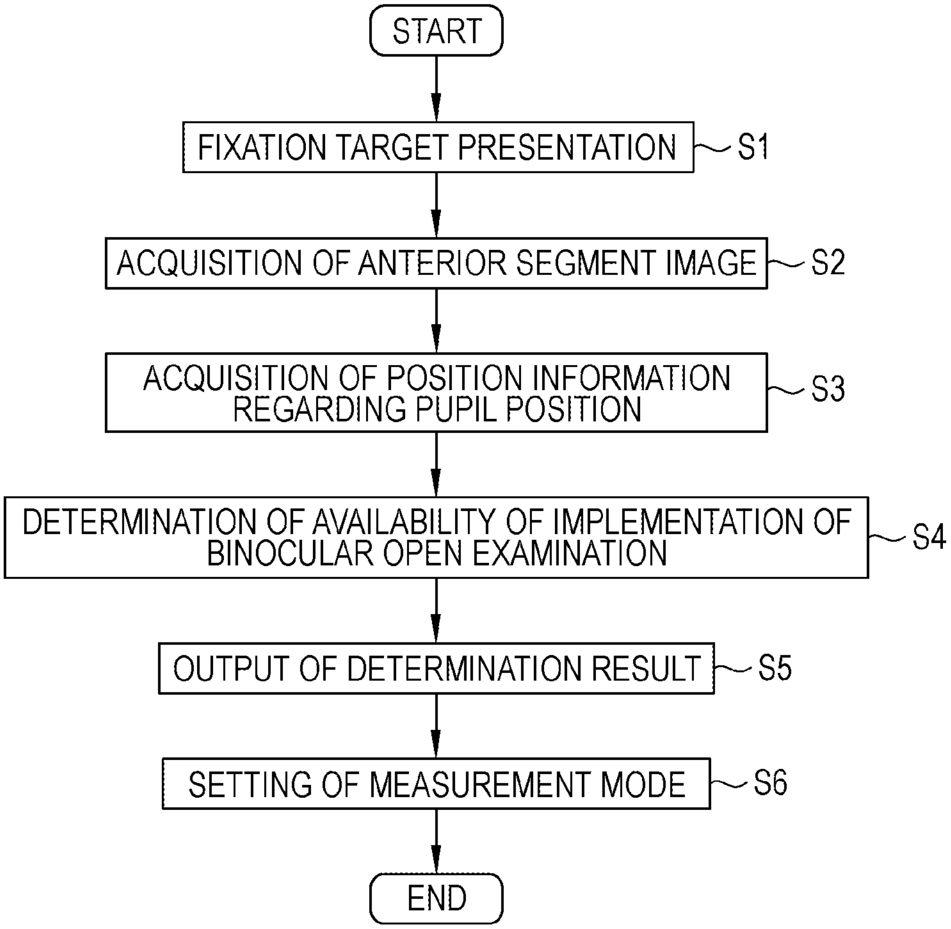
FIG. 8 is a flowchart of control operation.

FIG. 8 is a flowchart of control operation in the present example. A case where the controller 70 performs the above-described control processing to determine whether or not subjective measurement in the binocular open state can be implemented (availability of binocular fusion by the examinee's right and left eyes) will be described below by way of example.

<Fixation Target Presentation (S1)>

For example, the controller 70 controls the display 31 provided at each of the left-eye measurer 7L and the right-eye measurer 7R, thereby displaying the fixation target and the background target. A case where a minimum visual acuity value target of the examinee's eye E is displayed as the fixation target will be described below by way of example. Note that the fixation target is not limited to the visual acuity value target as long as the examinee's eye E can be fixated. For example, the controller 70 may display, as the fixation target, a graphic or a point image on the display 31.

For example, in a case where the minimum visual acuity value target of the examinee's eye E is displayed as the fixation target, the controller 70 displays, on the monitor 4, a visual acuity value setting screen for setting a visual acuity value. The examiner operates the monitor 4 to switch the visual acuity value target displayed on the display 31. Further, the examiner asks the examinee about whether or not the visual acuity value target is visible. The examinee observes the visual acuity value target in a state in which the fields of vision of the examinee's left eye EL and the examinee's right eye ER are open (i.e., the binocular open state), and responds to the inquiry from the examiner. In this way, the examiner determines the minimum visual acuity value of the examinee's eye E, thereby determining the visual acuity value target displayed on the display 31. Note that the controller 70 may be configured to display a prefixed visual acuity value target (e.g., a target with a visual acuity value of 0.7) on the display 31.

<Acquisition of Anterior Segment Image (S2)>

For example, the anterior segment of the measurement target eye is imaged in a state in which the examinee's left eye EL and the examinee's right eye ER are fixated to the fixation target displayed on the display 31. Moreover, the controller 70 determines the visual line direction of the measurement target eye by means of the anterior segment image of the measurement target eye captured in the binocular open state and the anterior segment image of the measurement target eye captured in the monocular covering state in which the field of vision of the unmeasured eye is covered.

Figure 9A:
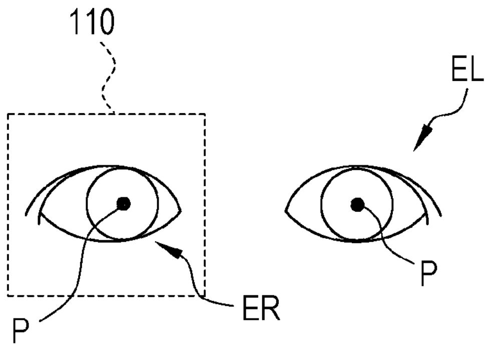
FIGS. 9A to 9C illustrate the visual line direction of an examinee's eye in a cover test.
Figure 9B:
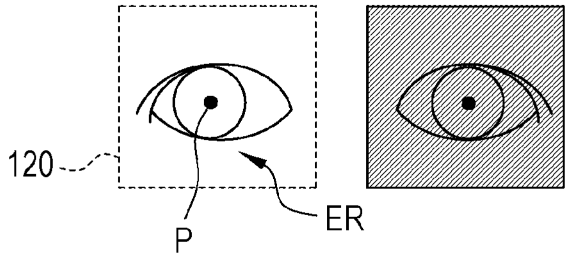
Figure 9C:
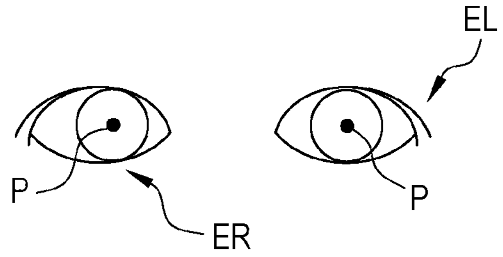

FIGS. 9A to 9C illustrate the visual line direction of the examinee's eye E. FIGS. 9A and 9C illustrate the visual line direction in the binocular open state in which the fields of vision of the examinee's right and left eyes are open. FIG. 9B illustrates the visual line direction of the examinee's right eye ER (the measurement target eye) in the monocular covering state in which the field of vision of the examinee's left eye EL (the unmeasured eye) is covered. In the state of FIG. 9A, the examiner operates an imaging switch displayed on the monitor 4. The controller 70 images the examinee's right eye ER (the measurement target eye) in accordance with an input signal from the monitor 4. Accordingly, an anterior segment image 110 of the measurement target eye in the binocular open state is acquired.

For example, the controller 70 controls, after having acquired the anterior segment image 110, the display 31 provided at the measurer 7 on the unmeasured eye side as described above, thereby bringing the monocular covering state in which the field of vision of the unmeasured eye is covered. In this state, the examiner again operates the imaging switch displayed on the monitor 4. The imaging optical system 100 images the examinee's right eye ER in the state of FIG. 9B. Accordingly, an anterior segment image 120 of the measurement target eye in the monocular covering state in which the field of vision of the unmeasured eye is covered is acquired. Thereafter, the fixation target is displayed on both of the displays 31 of the left-eye measurer 7L and the right-eye measurer 7R, and the binocular open state illustrated in FIG. 9C is brought back. Note that the anterior segment image of the measurement target eye may include the anterior segment image of the measurement target eye in the binocular open state and the anterior segment image of the measurement target eye in the monocular covering state. The controller 70 may acquire the anterior segment image in the states of FIGS. 9C and 9B. Moreover, in the present example, the imaging switch is, by way of example, displayed on the monitor 4. An imaging switch different from that on the monitor 4 may be connected to the subjective optometry apparatus 1.

Note that although not described in the present example, similar control processing (capturing of the anterior segment image) using the examinee's left eye EL as the measurement target eye may be performed after the above-described control processing has been performed for the examinee's right eye ER. Needless to say, such control processing may be implemented starting from any of the examinee's eyes.

<Acquisition of Position Information Regarding Pupil Position (S3)>

For example, the controller 70 performs the analysis processing of the image (i.e., the anterior segment image 110) of the measurement target eye captured in the binocular open state, thereby detecting the pupil position of the measurement target eye. Further, the controller 70 in the present example performs the analysis processing of the image (i.e., the anterior segment image 120) of the measurement target eye captured in the monocular covering state in which the field of vision of the unmeasured eye is covered, thereby detecting the pupil position of the measurement target eye, for example. For example, in the present example, the controller 70 may detect a pupil center position as the pupil position of the examinee's eye E. Note that any position of a pupil portion may be detected as the pupil position of the examinee's eye E. The anterior segment image 110 corresponds to one example of a first anterior segment image. The anterior segment image 120 corresponds to one example of a second anterior segment image.

For example, the controller 70 detects the pupil position of the examinee's eye E as a coordinate position on the anterior segment image, thereby acquiring the position information on the examinee's eye E (the pupil position of the examinee's eye E). For example, in the present example, the controller 70 acquires, as the position information on the detected pupil position, the pixel coordinates of the pupil position on the anterior segment image 110 and the anterior segment image 120. Moreover, the controller 70 obtains a difference in these pixel coordinates, thereby calculating the amount of movement of the pupil position of the examinee's eye E (the visual line direction), for example. Accordingly, the controller 70 acquires the position information on the pupil position (the visual line direction) of the examinee's eye E based on the anterior segment images captured by the imaging optical system 100.

Note that movement (and the movement amount) of the pupil position of the examinee's eye E is equivalent to movement (and the movement amount) of the visual line direction of the examinee's eye E. Moreover, the difference in the pixel coordinates between the pupil position (the pupil center position) on the anterior segment image 110 captured in the binocular open state and the pupil position (the pupil center position) on the anterior segment image 120 captured in the monocular covering state corresponds to the amount of movement of the pupil position (the pupil center position) between both states. Such a movement amount will be hereinafter referred to as a "pupil movement amount." The pupil movement amount corresponds to one example of the position information.

Figure 10A:
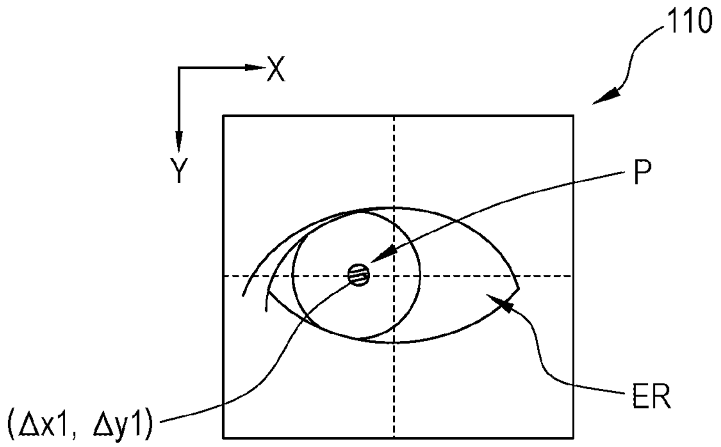
FIGS. 10A and 10B illustrate an anterior segment image of the examinee's eye.
Figure 10B:
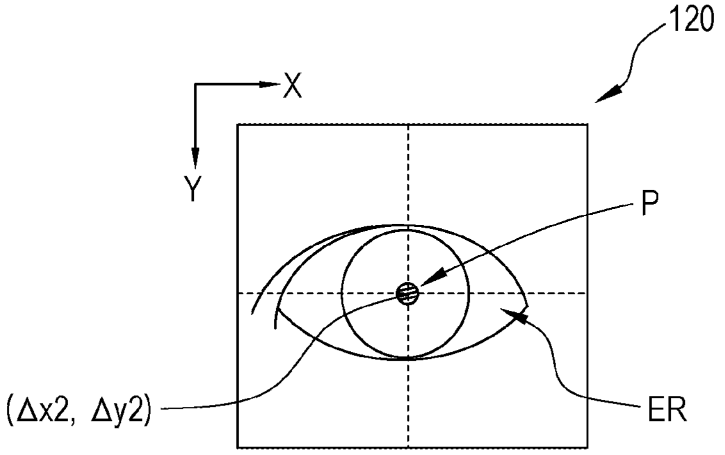

FIGS. 10A and 10B are views of the anterior segment images of the examinee's eye E. FIG. 10A is the anterior segment image 110 of the examinee's right eye ER (the measurement target eye) captured in the binocular open state. FIG. 10B is the anterior segment image 120 of the examinee's right eye ER captured in the monocular covering state in which the field of vision of the examinee's left eye EL (the unmeasured eye) is covered. For example, as will be seen from FIGS. 10A and 10B, when the measurement state is switched from the binocular open state in which the fields of vision of both eyes are open to the monocular covering state in which the field of vision of the examinee's left eye EL is covered, the examinee's right eye ER moves outward as viewed from the examiner, and the pupil position (the visual line direction) changes.

For example, the pixel coordinates of the pupil position of the examinee's right eye ER on the anterior segment image 110 illustrated in FIG. 10A are $\Delta x1$ in the X-direction and $\Delta y1$ in the Y-direction, and the pixel coordinates of the pupil position of the examinee's right eye ER on the anterior segment image 120 illustrated in FIG. 10B are $\Delta x2$ in the X-direction and $\Delta y2$ in the Y-direction. In this case, the controller 70 recognizes that the pupil position (the coordinate position of the pupil) on the anterior segment image 110 and the pupil position (the coordinate position of the pupil) on the anterior segment image 120 are different from each other, i.e., the position information on the examinee's right eye ER changes. Moreover, the controller 70 calculates the amounts of change (the pixel amount) in the pupil position of the examinee's right eye ER in the X-direction and the Y-direction, thereby obtaining the movement amount of the pupil position (the pupil movement amount). For example, the controller 70 calculates, as described above, the pupil movement amount when the measurement state is switched from the binocular open state to the monocular covering state. Note that the controller 70 in the present example may be configured to determine the direction of changing the visual line at the pupil position based on the difference in the pixel coordinates, for example.

<Determination on Availability of Implementation of Binocular Open Examination (S4)>

Next, the controller 70 determines whether or not subjective measurement in the binocular open state of the examinee's right and left eyes can be implemented. For example, the controller 70 determines whether or not subjective measurement in the binocular open state can be implemented in such a manner that the obtained pupil movement amount is compared with standard data. For example, the standard data is the pixel coordinate difference indicating a state allowing binocular vision, i.e., the pupil movement amount (a standard pupil movement amount) of the examinee's eye capable of performing binocular vision. That is, the standard data may be, for example, data indicating that the pixel coordinate difference (the pupil movement amount) is zero (i.e., the pupil position does not move between the binocular open state and the monocular covering state). Alternatively, the standard data may be data indicating the upper limit (a threshold for the pupil movement amount) of the pupil movement amount of the examinee's eye E capable of performing binocular vision, for example. For example, such data is obtained by statistical processing for multiple pupil movement amounts of the examinee's eyes.

For example, the controller 70 determines, in accordance with the pupil movement amount, availability of implementation of subjective measurement in the binocular open state. For example, the controller 70 detects the probability of difficulty in binocular vision by the examinee's eyes E in a case where the calculated pupil movement amount exceeds the preset threshold, and determines that it is difficult to implement subjective measurement in the binocular open state. Moreover, the controller 70 detects, in a case where the pupil movement amount is within the preset threshold, that binocular vision by the examinee's eyes E can be performed, and determines that subjective measurement in the binocular open state can be implemented, for example. Note that the subjective optometry apparatus 1 may be configured so that the examiner can change the above-described threshold to any value.

With this configuration, the controller 70 can acquire, as determination information 140, a determination result 130 and/or guide information 131 (see FIGS. 11A and 11B), for example. For example, the determination result 130 is a result of determination on whether or not subjective measurement in the binocular open state can be implemented. That is, the determination result 130 indicates availability of binocular vision. Moreover, the guide information 131 is guide information for guiding the examiner to the measurement mode of either the covering mode for performing subjective examination for one of the examinee's right and left eyes with the other eye being covered or the binocular open mode for performing subjective examination for one eye in the binocular open state. The guide information is the information for showing the examiner a recommended measurement mode. The controller 70 generates the guide information based on the determination result, for example.

For example, the controller 70 may be configured to acquire (generate) the determination result 130 as the determination information 140, or may be configured to acquire (generate) the guide information 131 as the determination information 140. Needless to say, the controller 70 may be configured to acquire both of the determination result 130 and the guide information 131 as the determination information 140. Note that in the present example, a case where the controller 70 acquires both of the determination result 130 and the guide information 131 as the determination information 140 will be described by way of example.

<Output of Determination Result (S5)>

Figure 11A:
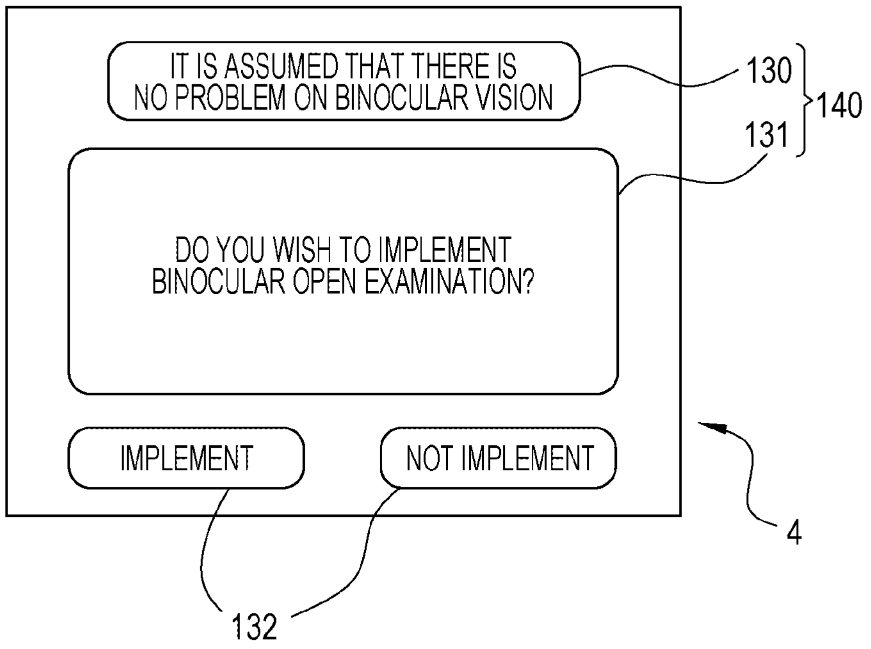
FIGS. 11A and 11B illustrate examples of determination information displayed on a monitor.
Figure 11B:
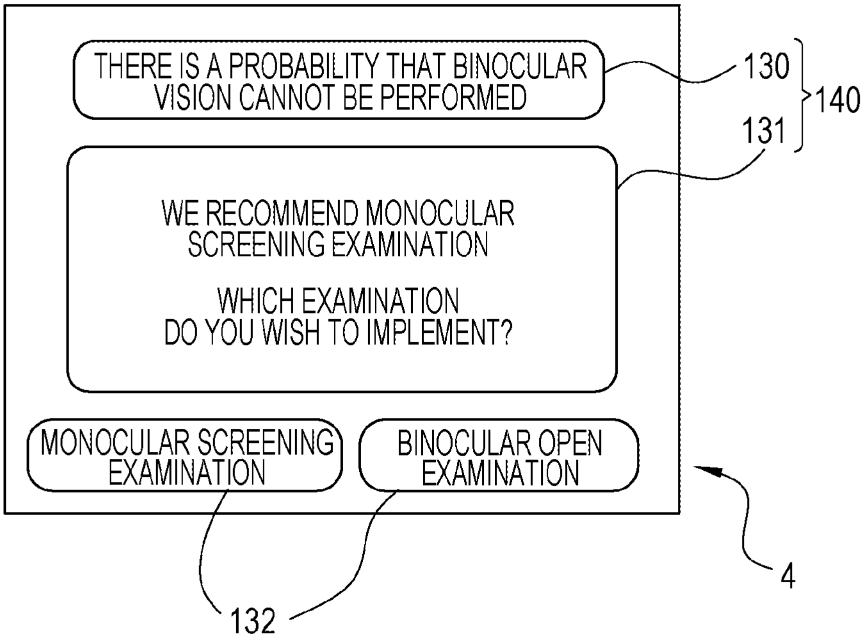

For example, the controller 70 outputs, to the monitor 4, the determination information regarding determination on whether or not subjective measurement can be implemented in the binocular open state. FIGS. 11A and 11B are views of examples of the determination information displayed on the monitor 4. For example, FIG. 11A illustrates a display screen when the examiner is guided to the measurement mode as the binocular open mode. FIG. 11B illustrates a display screen when the examiner is guided to the measurement mode as the covering mode. For example, the determination information 140 in the present example includes the determination result 130 indicating availability of binocular vision, and the guide information (a message) 131 for guiding the examiner to a specific measurement mode. Moreover, in the present example, the controller together displays, on the monitor 4, the determination information 140 and a mode selection switch 132 for selecting the measurement mode, for example.

For example, in the present example, in a case where the controller 70 determines that subjective measurement in the binocular open state can be implemented, the controller 70 displays the determination information 140 illustrated in FIG. 11A on the monitor 4. In this case, the indication of no problem on binocular vision by the examinee's eyes E is displayed as the determination result 130, for example. In this case, subjective measurement in the binocular open state is preferably implemented. Thus, a message (e.g., "Do you wish to implement binocular open examination?") for guiding the examiner to the measurement mode as the binocular open mode is displayed as the guide information 131. For example, the examiner identifies the guide information 131, and operates the mode selection switch 132. For example, in the present example, the mode selection switch 132 for asking whether the binocular open examination is to be "implemented" or is "not to be implemented" is displayed. The examiner can select to "implement" the examination, thereby setting the measurement mode to the binocular open mode.

Moreover, in the present example, in a case where the controller 70 determines that it is difficult to implement subjective measurement in the binocular open state, the controller 70 displays the determination information 140 illustrated in FIG. 11B on the monitor 4, for example. In this case, the indication of the probability of difficulty in binocular vision by the examinee's eyes E is displayed as the determination result 130, for example. In this case, subjective measurement in the monocular covering state is preferably implemented. Thus, the controller 70 displays, as the guide information 131, a message (e.g., "We recommend monocular covering examination") for guiding the examiner to the measurement mode as the covering mode. Moreover, a message (e.g., "Which examination do you wish to implement?") for asking which one of the covering mode or the binocular open mode is to be implemented is displayed as the guide information 131. For example, the examiner identifies the guide information 131, and operates the mode selection switch 132. For example, in the present example, the mode selection switch 132 for asking which one of the monocular covering examination or the binocular open examination is to be implemented is displayed, for example. The examiner can select the "monocular covering examination," thereby setting the measurement mode to the covering mode. Note that even in a case where the controller 70 detects, for example, the probability of difficulty in binocular vision by the examinee's eyes E, the examiner may select the binocular open mode. For example, in this case, the examiner can select the "binocular open examination" of the mode selection switch 132, thereby setting the measurement mode to the binocular open mode.

<Setting of Measurement Mode (S6)>

When the examiner operates the mode selection switch 132 to select the measurement mode, the controller 70 controls the subjective measurer in accordance with the selected measurement mode. For example, the controller 70 controls, in accordance with the selected measurement mode, at least any of various members forming the measurer 7. Accordingly, default setting of various members in the binocular open mode or the covering mode can be performed. For example, in the present example, the case of selecting the binocular open mode and the case of selecting the covering mode are sequentially described.

For example, in the case of selecting the binocular open mode, examination for the eyes is performed one by one in the binocular open state. For example, the examiner operates the monitor 4 to select the examinee's eye (e.g., the examinee's right eye ER) to be first measured. For example, the controller 70 controls the display 31 of each of the left-eye measurer 7L and the right-eye measurer 7R, thereby projecting the target onto both of the examinee's left eye EL and the examinee's right eye ER. Note that in examination for one eye, the examinee's eye to be first measured may be any of the examinee's right and left eyes.

For example, the controller 70 displays an examination target such as a Landolt ring target and a white background target on the display 31 on an examinee's right eye ER (measurement target eye) side. Moreover, the controller 70 displays a white background target on the display 31 on an examinee's left eye EL (unmeasured eye) side, for example. Note that the examination target is not limited to the Landolt ring target, and may be other examination targets. Moreover, the background target is not limited to the white background target, and may be other background targets. Accordingly, the examination target is visible by the examinee's right eye ER, but is not visible by the examinee's left eye EL. That is, the examiner can start, in the binocular open state in which both eyes are open without the unmeasured eye being covered, subjective measurement for the examinee's right eye ER (the measurement target eye), thereby acquiring the optical characteristics (the optical characteristic results) of the examinee's right eye ER. Note that although not described in the present example, the examiner may project, as in description above, the examination target onto the examinee's left eye EL to acquire the optical characteristics of such an eye.

For example, in the case of selecting the covering mode, a state in which the field of vision of the unmeasured eye is covered is brought. For example, the controller 70 controls the display 31 provided at the left-eye measurer 7L as described above such that no examination target and background target are projected onto the examinee's left eye EL (the unmeasured eye). Accordingly, the examinee is in such a state that the field of vision of the examinee is covered on the unmeasured eye side. Moreover, the controller 70 displays the examination target and the background target on the display 31 provided at the right-eye measurer 7R, and only projects the examination target onto the examinee's right eye ER (the measurement target eye), for example. For example, the examiner can start, in such a monocular covering state, subjective measurement for the examinee's right eye ER (the measurement target eye), and can acquire the optical characteristics (the optical characteristic results) of the examinee's right eye ER. Note that although not described in the present example, the examiner may cover, as in description above, the field of vision of the examinee's right eye ER to acquire the optical characteristics of the examinee's left eye EL.

As described above, the subjective optometry apparatus 1 in the present example has the controller 70, for example. The controller 70 functions as an acquisitor configured to acquire the position information on at least one of the examinee's right and left eyes, a determiner configured to acquire the determination information by determining whether or not subjective measurement in the binocular open state of the examinee's right and left eyes can be implemented, and a determination information output unit configured to output the determination information. Thus, even if the examiner has no knowledge regarding the examinee's eye, the examiner identifies the output determination information so that subjective measurement can be performed after determination on whether or not the binocular open examination for the examinee's eye is to be performed has been easily made.

For example, in the subjective optometry apparatus 1 of the present example, the controller 70 functions as a setter. The setter receives the determination information output from the determination information output unit, thereby setting, based on the determination information, the measurement mode either to any of the covering mode or to the binocular open mode. In the covering mode, subjective examination for one of the examinee's right and left eyes is performed with the other eye being covered. In the binocular open mode, subjective examination is performed for one eye in the binocular open state. Moreover, in the subjective optometry apparatus 1 of the present example, the controller 70 functions as a drive controller configured to control the subjective measurer in accordance with the set measurement mode. With this configuration, a proper measurement mode is set in accordance with the state of binocular vision by the examinee's eyes. Thus, the probability of selecting an erroneous measurement mode by the examiner is reduced, and therefore, subjective measurement can be accurately performed.

For example, in the subjective optometry apparatus 1 of the present example, the controller 70 (the determiner) acquires the determination result as the determination information. That is, the controller 70 acquires the determination result indicating whether or not favorable binocular vision can be performed by the examinee's eyes, for example. Thus, the examiner refers to the determination result so that the state of binocular vision by the examinee's eyes can be easily determined.

For example, in the subjective optometry apparatus 1 of the present example, the controller 70 (the determiner) acquires the guide information as the determination information. The guide information is the information for guiding the examiner to the measurement mode of either the covering mode for performing subjective examination for one of the examinee's right and left eyes with the other eye being covered or the binocular open mode for performing subjective examination for one eye in the binocular open state. Thus, the examiner refers to the guide information so that a proper measurement mode can be selected in accordance with the examinee's eye.

For example, the subjective optometry apparatus 1 in the present example is configured such that the controller 70 (the determination information output unit) displays the determination information on the monitor 4 (a display). Thus, the examiner refers to the displayed determination information so that the state of the examinee's eye can be easily recognized.

For example, the subjective optometry apparatus 1 in the present example includes the anterior segment imaging optical system 100 (an anterior segment acquisitor) configured to acquire the anterior segment image of at least one of the examinee's right and left eyes. Moreover, in the subjective optometry apparatus 1 of the present example, the controller 70 (the acquisitor) analyzes the anterior segment image acquired by the anterior segment imaging optical system 100 (the anterior segment acquisitor), thereby acquiring the position information on the examinee's eye. Thus, the examiner can easily obtain the position information on the examinee's eye based on the anterior segment image of the examinee's eye. Moreover, the examiner can easily determine (acquire) movement of the visual line direction of the examinee's eye based on the change in the position information.

Note that the anterior segment imaging optical system 100 may acquire the first anterior segment image as the anterior segment image of at least one (an examinee's imaging target eye) of the examinee's right eye ER and the examinee's left eye EL in a case (the binocular open state) where both of the examinee's right and left eyes are in the uncovered state. Further, the anterior segment imaging optical system 100 may acquire the second anterior segment image as the anterior segment image of the examinee's imaging target eye in a case (the monocular covering state) where one of the examinee's eyes is in the covered state. In this case, the controller 70 (the acquisitor) may analyze the first anterior segment image and the second anterior segment image, thereby acquiring the position information (e.g., the pupil movement amount) on the examinee's imaging target eye. Note that the examinee's imaging target eye may be one eye or both eyes.

For example, in the subjective optometry apparatus 1 of the present example, the controller 70 (the acquisitor) detects the pupil position of the examinee's eye to acquire the position information based on the detected pupil position. Accordingly, movement of the examinee's eye can be determined with a simple configuration.

For example, the subjective optometry apparatus 1 in the present example has the right-left pair of the examinee's right-eye corrective optical system 60 and the examinee's left-eye corrective optical system 60. It is configured such that the examinee's right-eye corrective optical system 60 and the examinee's left-eye corrective optical system 60 are position-adjusted to the examinee's right eye ER and the examinee's left eye EL, respectively. Thus, position adjustment of each corrective optical system with respect to a corresponding one of the examinee's right and left eyes can be correctly implemented.

Moreover, in the subjective optometry apparatus 1, the controller 70 (the acquisitor) detects, as described later, at least any of first position information as the position information on the examinee's right-eye corrective optical system 60 obtained when the examinee's right-eye corrective optical system 60 is position-adjusted to the examinee's right eye ER and second position information as the position information on the examinee's left-eye corrective optical system 60 obtained when the examinee's left-eye corrective optical system 60 is position-adjusted to the examinee's left eye EL. Further, the controller 70 (the acquisitor) acquires the position information on the examinee's eye E based on at least any of the detected first position information and the detected second position information. Accordingly, the position information on the corrective optical system position-adjusted to a measurement position in subjective measurement is utilized so that the position information on the examinee's eye can be accurately acquired.

<Modifications>

In the above-described example, a case where the anterior segment images of the examinee's eye E are captured in such a manner that the control processing is performed while the cover test is being replicated has been described by way of example. However, the technique of capturing the anterior segment image is not limited to above. For example, the anterior segment image of the examinee's eye E may be captured by the control processing performed while a cover-uncover test is being replicated. The cover-uncover test is the following examination method. That is, in this test, both eyes of the examinee are fixated to the fixation target. In this state, the measurement target eye is temporarily covered, and movement of the measurement target eye after having been uncovered is specified. For example, in this case, the controller 70 controls the display state of the display 31 provided at the measurer 7 on the measurement target eye side, thereby switching the measurement state between the binocular open state and the monocular covering state. For example, the imaging optical system 100 images the measurement target eye right after the covered measurement target eye has been uncovered and after a lapse of several seconds after uncovering of the covered measurement target eye.

In the above-described example, a case where the imaging optical system 100 images at least one of the examinee's right and left eyes to acquire the anterior segment image of such an eye has been described by way of example. However, the technique of capturing the anterior segment image is not limited to above. For example, the imaging optical system 100 may sequentially image the examinee's left eye EL and the examinee's right eye ER, thereby acquiring the anterior segment image of each examinee's eye. Alternatively, the imaging optical system 100 may simultaneously image the examinee's left eye EL and the examinee's right eye ER, thereby acquiring the anterior segment image of each examinee's eye, for example. In this case, the cover test and the cover-uncover test can be simultaneously implemented for the examinee's eye E. As another alternative, the imaging optical system 100 may be configured to image both of the examinee's left eye EL and the examinee's right eye ER as the anterior segment images of the examinee's eyes E, thereby acquiring a single anterior segment image including the anterior segment image of the examinee's left eye EL and the anterior segment image of the examinee's right eye ER. Alternatively, the imaging optical system 100 may be configured to separately image the examinee's left eye EL and the examinee's right eye ER, thereby acquiring the anterior segment images of both eyes one by one. Note that the imaging optical system 100 may be configured to acquire the anterior segment image in real time, for example.

In the above-described example, a case where the imaging optical system 100 captures the anterior segment image of the examinee's eye has been described by way of example. However, the member configured to capture the anterior segment image is not limited to the imaging optical system 100. For example, the observing optical system 50 provided at the measurer 7 can acquire the anterior segment image of the examinee's eye. That is, the examinee's left eye EL may be imaged by the observing optical system 50 provided at the left-eye measurer 7L. Moreover, the examinee's right eye ER may be imaged by the observing optical system 50 provided at the right-eye measurer 7R.

In the above-described example, a case where the imaging optical system 100 images the anterior segment of the examinee's eye E in accordance with operation of the imaging switch by the examiner has been described by way of example. However, the technique of capturing the anterior segment image is not limited to above. For example, the anterior segment of the examinee's eye E may be automatically imaged. For example, in this case, the imaging optical system 100 may automatically capture the anterior segment image of the measurement target eye in association with switching of the display state of the display.

In the above-described example, a case where the imaging optical system 100 acquires the anterior segment image of the examinee's eye E has been described by way of example. However, the target for imaging by the imaging optical system 100 is not limited to above. For example, the imaging optical system 100 may only need to acquire at least the anterior segment image of the examinee's eye E. That is, the image acquired by the imaging optical system 100 may be a facial image obtained by imaging of the entire face of the examinee.

In the above-described example, a case where the control processing performed while the cover test is being replicated is performed once has been described by way of example. However, the number of times of the control processing is not limited to one time. For example, such control processing may be performed multiple times. In this case, the controller 70 acquires the anterior segment images of the examinee's eye E in the monocular covering state and the binocular open state multiple times, thereby obtaining the pupil movement amount by means of each anterior segment image. For example, in a case where the control processing is performed three times while the cover test is being replicated, the pupil movement amount is obtained three times. For example, based on the multiple obtained pupil movement amounts, the controller 70 may determine, in a comprehensive way, whether or not the binocular open examination can be implemented for the examinee's eye E.

In the above-described example, a case where the controller 70 determines (acquires) movement of the examinee's eye E based on the anterior segment image of the examinee's eye E to determine whether or not the binocular open examination can be implemented has been described by way of example. However, such a determination technique is not limited to above. For example, the controller 70 may be configured to determine, based on movement of the examinee's eye E observed by the examiner, whether or not the binocular open examination can be implemented. In this case, illustrations etc. indicating movement of the examinee's eye may be displayed as a list on the monitor 4, for example. For example, the examiner implements the cover test etc. for the examinee's eye E, thereby observing movement of the examinee's eye E. Moreover, the examiner selects an illustration consistent with observed movement of the examinee's eye E from the illustrations displayed on the monitor 4. For example, the controller 70 determines, based on the information input as described above and indicating movement of the examinee's eye E, whether or not the binocular open examination can be implemented.

In the above-described example, a case where the controller 70 detects the pupil position of the examinee's eye E based on the anterior segment images to acquire the position information on the examinee's eye E has been described by way of example. However, the technique of acquiring the position information on the examinee's eye E is not limited to above. For example, the controller 70 may be configured to detect the iris position etc. of the examinee's eye E, thereby acquiring the position information on the examinee's eye E. For example, the controller 70 can also acquire the position information on the examinee's eye E by detecting the corneal apex position of the examinee's eye E. In this case, the controller 70 performs the analysis processing for the anterior segment images, thereby detecting the corneal apex position of the examinee's eye E, for example. Moreover, the controller 70 acquires the position information on the examinee's eye E based on the detected corneal apex position. Note that the controller 70 can specify the corneal apex position by projecting the target image onto the cornea of the examinee's eye E and detecting the position of such a target image.

In the above-described example, a case where the pixel coordinate difference (the pupil movement amount) is used as the standard data has been described by way of example. However, the standard data is not limited to above. For example, the controller 70 may be configured to use, as the standard data, the anterior segment images captured by the imaging optical system 100. In this case, the controller 70 detects displacement of the anterior segment of the examinee's eye E by means of the anterior segment images. For example, the controller 70 may overlap the anterior segment image 120 as the reference data with the anterior segment image 110 as the standard data, thereby detecting displacement of the anterior segment. With such a configuration, the controller 70 can determine whether or not the pupil position on the anterior segment image 110 and the pupil position on the anterior segment image 120 are coincident with each other, for example. Moreover, the controller 70 can determine, in accordance with such displacement of the anterior segment, availability of implementation of subjective measurement in the binocular open state, for example. Note that the controller 70 may overlap the anterior segment image 120 as the standard data and the anterior segment image 110 as the reference data with each other, thereby detecting displacement of the anterior segment, for example.

In the above-described example, a case where the determination result 130 and the guide information (the message) 131 are displayed as the determination information has been described by way of example. However, the determination information is not limited to above. For example, the controller 70 may only need to display the determination information to guide the examiner to a proper measurement mode. That is, the determination information may only need to include at least the guide information (the message) 131. For example, the guide information (the message) 131 may include display contents for asking about whether or not the binocular open examination is to be implemented or whether or not the monocular covering examination is to be implemented. The guide information (the message) 131 may include display contents for warning that there is a problem in implementation of the binocular open examination.

In the above-described example, a case where the controller 70 displays the determination information on the monitor 4 has been described by way of example. However, the display form of the determination information is not limited to above. For example, the determination information may be printed out. In this case, the controller 70 may be configured to output (transfer) the determination information to a printer etc. via wireless communication or a communication cable. Alternatively, a main body of the subjective optometry apparatus 1 may include the printer etc., and the controller 70 may print out the determination information by means of the printer. As another alternative, the controller 70 may transmit, as data, the determination information to various members (e.g., the measurer 7), for example. In this case, various members are controlled based on the received data.

In the above-described example, a case where the examiner operates the mode selection switch 132 to set the measurement mode either to the binocular open mode or to the covering mode has been described by way of example. However, the technique of setting the measurement mode is not limited to above. For example, the controller 70 may be configured to automatically set the measurement mode based on the determination information regarding determination on whether or not subjective measurement in the binocular open state can be implemented. In this case, the controller 70 automatically sets the measurement mode to the binocular open mode in the case of determining, without any problem of binocular vision by the examinee's eyes E, that subjective measurement in the binocular open state can be implemented, for example. Moreover, in a case where there is a probability that binocular vision by the examinee's eyes E is difficult and it is determined that it is difficult to implement subjective measurement in the binocular open state, the controller 70 automatically sets the measurement mode to the covering mode, for example. For example, the controller 70 receives the determination information to set the measurement mode as described above.

In the case of selecting the binocular open mode, the controller 70 may fog the unmeasured eye. In this case, the controller 70 controls the displays 31 provided at the left-eye measurer 7L and the right-eye measurer 7R, thereby projecting the examination target onto the measurement target eye and the unmeasured eye. Moreover, the controller 70 uses, e.g., the target visual acuity value of the fogged examinee's eye E to calculate the amount of fogging of the unmeasured eye. For example, the controller 70 adds the calculated fogging amount to an objective value acquired in objective measurement, thereby changing the position of the display 31 provided at the measurer on the unmeasured eye side. Accordingly, the measurement target eye can observe a correct examination target, and the unmeasured eye can observe the examination target blurred by fogging.

The corrective optical system 60 in the above-described example may be an optometry unit (a phoropter) configured to switch the optical element disposed in front of the examinee's eye E. For example, the optometry unit may have a lens disc including a plurality of optical elements disposed on the same circumference and a driver configured to rotate the lens disc. Further, the optometry unit may include the member configured to electrically switch the optical element by driving of the driver (e.g., a motor).

For example, the corrective optical system 60 in the above-described example may have an optical element disposed between an optical member configured to guide the target light flux from the light projecting optical system to the examinee's eye and the light source of the light projecting optical system. Further, the corrective optical system may be configured to control the optical elements to change the optical characteristics of the target light flux. That is, the corrective optical system (a corrector) may be configured similar to a phantom lens refractometer (a phantom corrective optical system). In this case, the target light flux corrected by the corrective optical system is guided to the examinee's eye through the optical member, for example.

In the above-described example, a case where the single deflecting mirror 81 is provided on each of the left-eye optical path and the right-eye optical path has been described by way of example. However, arrangement of the deflecting mirror is not limited to above. A plurality of deflecting mirrors may be provided on each of the left-eye optical path and the right-eye optical path. For example, two deflecting mirrors may be provided on each of the left-eye optical path and the right-eye optical path. Alternatively, two deflecting mirrors may be provided on either the left-eye optical path or the right-eye optical path. For example, two deflecting mirrors may be provided on the left-eye optical path. In the case of providing two deflecting mirrors on a single optical path, it may be configured such that one of the deflecting mirrors is rotatably moved in the X-direction and the other deflecting mirror is rotatably moved in the Y-direction. For example, the deflecting mirrors 81 are rotatably moved to deflect an apparent light flux for forming the image of the corrective optical system 60 in front of the examinee's eye E. Accordingly, an image formation position can be optically corrected.

Figure 12:
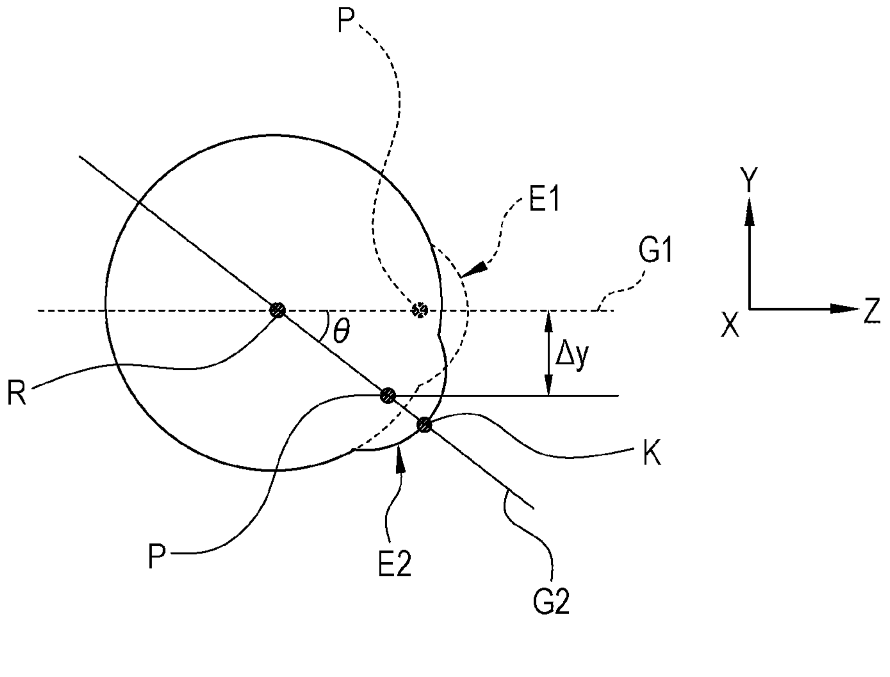
FIG. 12 is a drawing for describing a modification of determination on availability of implementation of subjective measurement in a binocular open state based on a prism amount.

In the above-described example, a case where availability of implementation of subjective measurement in the binocular open state is determined in accordance with the movement amount (the pupil movement amount) of the pupil position obtained from the pixel coordinates of the pupil position on the anterior segment image 110 and the anterior segment image 120 has been described by way of example. However, the technique of determining availability of implementation of subjective measurement in the binocular open state is not limited to above. For example, in the subjective optometry apparatus 1, the controller 70 may be configured to calculate the prism amount of the examinee's eye E by means of the pupil movement amount and determine availability of implementation of subjective measurement in the binocular open state based on the prism amount. FIG. 12 is a view for describing a modification of determination on availability of implementation of subjective measurement in the binocular open state based on the prism amount. For example, in an example illustrated in FIG. 12, the visual line direction G1 of an examinee's eye E1 indicated by a dashed line moves to the visual line direction G2 of an examinee's eye E2 indicated by a solid line, and the pupil position P of the examinee's eye moves downward. Note that in the present example, description will be made focusing on the movement amount of the pupil position P in the Y-direction. In the case of determining availability of implementation of subjective measurement based on the prism amount, the controller 70 may first utilize the following arithmetic formula to obtain the pivot angle θ of the examinee's eye.

$$\theta=\tan^{-1}(\Delta y/(r-p))$$

For example, the pivot angle θ of the examinee's eye can be represented using the movement amount Δy of the pupil position P in the Y-direction in the case of viewing the examinee's eye from the front, a distance r (e.g., 13 mm) from the pivot center R to the corneal apex position K of the examinee's eye, and a distance p (e.g., 3 mm) from the pupil position P to the corneal apex position K. For example, the controller 70 substitutes, into the above-described arithmetic formula, the movement amount Δy obtained from the pixel coordinates of the pupil position on the anterior segment image 110 and the anterior segment image 120, thereby calculating the pivot angle θ of the examinee's eye E.

In the example illustrated in FIG. 12, a case where the movement amount of the pupil position P in the Y-direction is used as the movement amount of the pupil position P has been described by way of example. However, the movement amount of the pupil position P used for calculation of the pivot angle θ of the examinee's eye E is not limited to above. For example, in addition to the movement amount of the pupil position P in the Y-direction, the controller 70 may take, as the movement amount of the pupil position P, the movement amount of the pupil position P in the Z-direction upon movement of the visual line direction of the examinee's eye from G1 to G2 into consideration.

In the example illustrated in FIG. 12, a case where the pupil position P of the examinee's eye moves downward has been described by way of example. Even in the case of moving the pupil position in any direction, the controller 70 can apply the above-described arithmetic formula to calculate the pivot angle θ. That is, even in a case where the visual line direction of the examinee's eye has moved in any of the up-down direction, the right-left direction, and the oblique direction, the controller 70 can calculate the pivot angle θ of the examinee's eye by means of the movement amounts of the pupil position P of the examinee's eye in the X-direction and the Y-direction. Needless to say, the controller 70 may take, as the movement amount of the pupil position P, the movement amount of the pupil position P in the Z-direction into consideration, as described above.

The controller 70 may obtain the above-described pivot angle θ of the examinee's eye by means of a Purkinje image formed by projection of the target image onto the cornea of the examinee's eye. In this case, the controller 70 can calculate the pivot angle θ of the examinee's eye based on a change in the position of the Purkinje image detected on the anterior segment image 110 and the anterior segment image 120, for example.

For example, the controller 70 may obtain the prism amount Δ of the examinee's eye in such a manner that the pivot angle θ calculated as described above is substituted into the following arithmetic formula.

$$\Delta=(\tan\theta/0.01)$$

For example, the controller 70 compares a preset threshold and the calculated prism amount of the examinee's eye E, thereby determining availability of implementation of subjective measurement in the binocular open state. For example, the controller 70 detects the probability of difficulty in binocular vision by the examinee's eyes E in a case where the prism amount of the examinee's eye E exceeds the preset threshold, and determines that it is difficult to implement subjective measurement in the binocular open state. Moreover, the controller 70 detects, in a case where the prism amount of the examinee's eye E is within the preset threshold, that binocular vision by the examinee's eyes E can be performed, and determines that subjective measurement in the binocular open state can be implemented, for example. For example, a predetermined value obtained by, e.g., experiment and/or simulation may be set as the threshold in advance. Moreover, the subjective optometry apparatus 1 may be configured so that the examiner can change the above-described threshold to any value in accordance with the state of the examinee's eye E, for example.

In the above-described example, a case where the controller 70 acquires the pupil position of the examinee's eye E detected based on the anterior segment images and acquires the position information on the pupil position has been described by way of example. However, the position information is not limited to above. For example, the controller 70 may be configured to acquire the position information on the corrective optical system 60 when the corrective optical system 60 is position-adjusted to the examinee's eye E.

That is, the controller 70 may detect at least any of first position information d1 as the position information on the examinee's right-eye corrective optical system 60 obtained when the examinee's right-eye corrective optical system 60 is position-adjusted to the examinee's right eye ER and second position information d2 as the position information on the examinee's left-eye corrective optical system 60 obtained when the examinee's left-eye corrective optical system 60 is position-adjusted to the examinee's left eye EL, and may acquire the position information on at least one of the examinee's right and left eyes based on at least any of the detected first position information d1 and the detected second position information d2. Based on the examinee's eye position information acquired as described above, the controller 70 may determine availability of implementation of subjective measurement in the binocular open state, i.e., whether or not subjective measurement in the binocular open state of the examinee's right and left eyes can be implemented. Alternatively, the controller 70 may determine, based on at least any of the first position information and the second position information, availability of implementation of subjective measurement in the binocular open state.

For example, the controller 70 acquires (detects) at least any of the first position information d1 and the second position information d2. Further, the controller 70 determines availability of implementation of subjective measurement in the binocular open state based on the acquired position information, for example. Needless to say, the controller 70 may be configured to acquire both of the first position information d1 and the second position information d2 to determine availability of implementation of subjective measurement in the binocular open state based on both types of the position information.

For example, the first position information d1 and the second position information d2 as the position information on the corrective optical system 60 may be the coordinate position of the corrective optical system 60, or may be the movement amount of the corrective optical system 60 (a change in the coordinate position). A case where the movement amount of the corrective optical system 60 is acquired as the first position information d1 and the second position information d2 will be described below by way of example.

Figure 13:
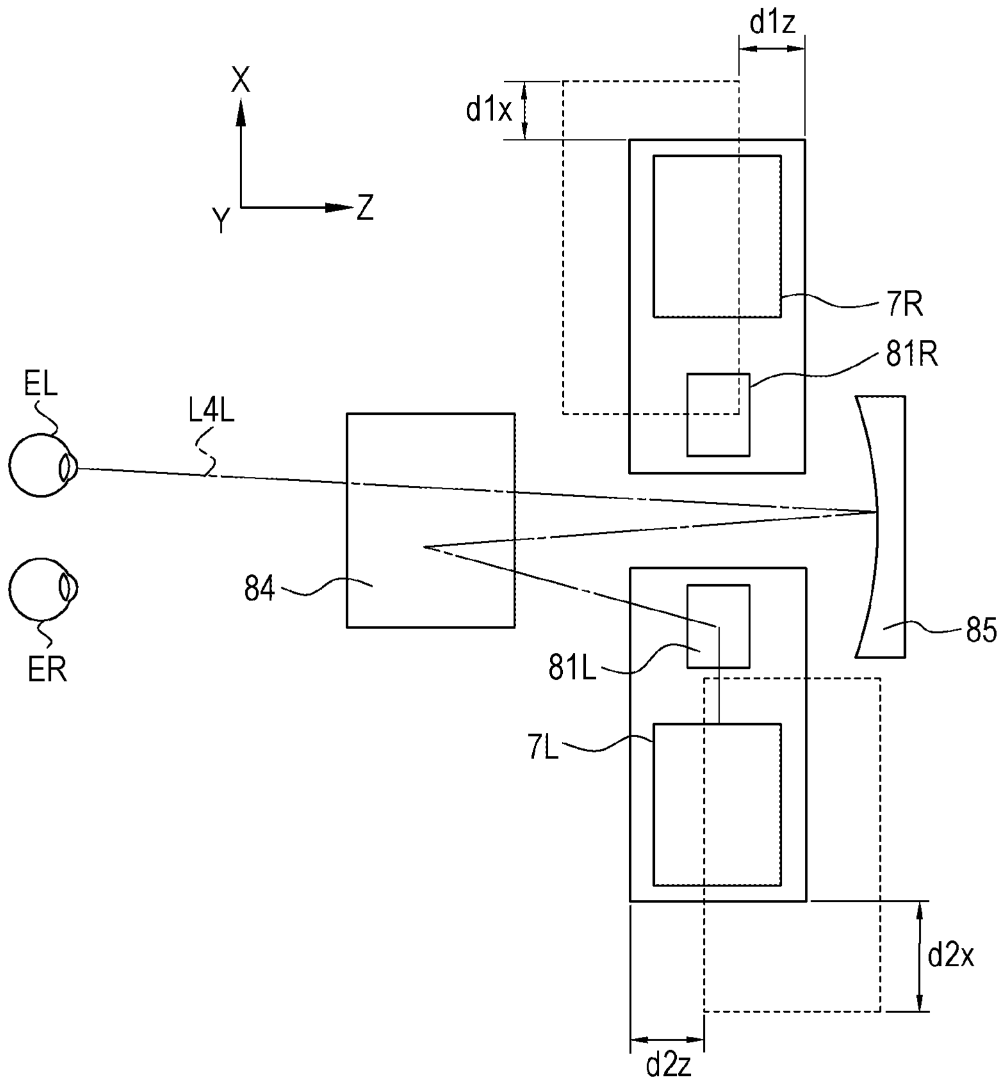
FIG. 13 is a drawing for describing a modification of acquisition of position information.

FIG. 13 is a view for describing a modification of acquisition of the position information on the corrective optical system 60. Note that as illustrated in FIG. 2, the corrective optical system 60 is provided at the measurer 7. Thus, the movement amount of the corrective optical system 60 can be obtained as the movement amount of the measurer 7 (and the deflecting mirror 81) as illustrated in FIG. 13. In an example illustrated in FIG. 13, the measurer 7 and the deflecting mirror 81 are integrally moved in position adjustment of the corrective optical system 60 with respect to the examinee's eye.

For example, the first position information d1 is obtained from a movement amount d1*x* and a movement amount d1*z*. The movement amount d1*x* is the movement amount of the measurer 7R and the deflecting mirror 81R in the X-direction in position adjustment of the corrective optical system 60 with respect to the examinee's right eye ER. The movement amount d1*z* is the movement amount of the measurer 7R and the deflecting mirror 81R in the Z-direction in position adjustment of the corrective optical system 60 with respect to the examinee's right eye ER.

For example, in the example illustrated in FIG. 13, the measurer 7R and the deflecting mirror 81R are integrally moved in the X-direction to perform position adjustment of the corrective optical system 60 with respect to the examinee's right eye ER in the right-left direction (the X-direction). Further, the measurer 7R and the deflecting mirror 81R are integrally moved in the Z-direction to perform position adjustment of the corrective optical system 60 with respect to the examinee's right eye ER in the up-down direction (the Y-direction).

Similarly, the second position information d2 is obtained from a movement amount d2*x* and a movement amount d2*z*, for example. The movement amount d2*x* is the movement amount of the measurer 7L and the deflecting mirror 81L in the X-direction in position adjustment of the corrective optical system 60 with respect to the examinee's left eye EL. The movement amount d2*z* is the movement amount of the measurer 7L and the deflecting mirror 81L in the Z-direction in position adjustment of the corrective optical system 60 with respect to the examinee's left eye EL.

For example, the controller 70 integrally moves the measurer 7R and the deflecting mirror 81R in each of the monocular covering state in which the field of vision of the examinee's left eye EL is covered and the binocular open state in which the fields of vision of the examinee's right eye ER and the examinee's left eye EL are open. Accordingly, the controller 70 performs position adjustment of the corrective optical system 60 with respect to the pupil position of the examinee's right eye ER.

In this state, the controller 70 obtains, in the monocular covering state, the movement amounts d1*x* and d1*z* of the measurer 7R and the deflecting mirror 81R from original positions. Moreover, the controller 70 obtains, in the binocular open state, the movement amounts d1$x$ and d1$z$ of the measurer 7R and the deflecting mirror 81R from the original positions. For example, the controller 70 calculates a difference between the movement amount d1$x$ and d1$z$ obtained in the monocular covering state and the movement amount d1$x$ and d1$z$ obtained in the binocular open state, thereby obtaining a difference value. The controller 70 compares such a difference value and a predetermined movement amount set as a threshold in advance, thereby determining availability of implementation of subjective measurement in the binocular open state.

That is, in a case where the above-described difference value (the difference in the movement amount of the pupil position) exceeds the preset threshold, the controller 70 detects the probability of difficulty in binocular vision by the examinee's eyes E, and determines that it is difficult to implement subjective measurement in the binocular open state, for example. Moreover, in a case where the above-described difference value is within the preset threshold, the controller 70 detects that binocular vision by the examinee's eyes E can be performed, and determines that subjective measurement in the binocular open state can be implemented, for example.

Note that in the above-described example, a case where the corrective optical system 60 is position-adjusted to the pupil position of the examinee's right eye ER has been described. For the examinee's left eye EL, the controller 70 can also implement position adjustment of the corrective optical system 60 similar to that for the examinee's right eye ER, thereby determining availability of implementation of subjective measurement in the binocular open state.

Note that the embodiment of the present disclosure may include the following first to eleventh subjective optometry apparatuses, the following first subjective optometry program, and the first subjective optometry method.

The first subjective optometry apparatus is a subjective optometry apparatus configured to subjectively measure optical characteristics of an examinee's eye, the subjective optometry apparatus including a subjective measurer which has a corrective optical system disposed on an optical path of a light projecting optical system configured to project a target light flux toward the examinee's eye and configured to change optical characteristics of the target light flux and which is configured to subjectively measure the optical characteristics of the examinee's eye; an acquisitor configured to acquire position information on at least one of the examinee's right and left eyes; a determiner configured to determine, based on the position information acquired by the acquisitor, whether or not subjective measurement can be implemented in a binocular open state of the examinee's right and left eyes, thereby acquiring determination information; and a controller configured to output the determination information acquired by the determiner.

The second subjective optometry apparatus is the first subjective optometry apparatus further including a setter configured to receive the determination information output by the controller and set, based on the determination information, a measurement mode either to a covering mode for performing subjective examination for one of the examinee's right and left eyes with the other eye being covered or to a binocular open mode for performing subjective examination for one eye in the binocular open state, and a drive controller configured to control the subjective measurer in accordance with the mode set based on the setter.

The third subjective optometry apparatus is the first subjective optometry apparatus in which the determiner acquires a determination result as the determination information.

The fourth subjective optometry apparatus is the first subjective optometry apparatus in which the determiner acquires, as the determination information, guide information for guiding either to the covering mode for performing subjective examination for one of the examinee's right and left eyes with the other eye being covered or to the binocular open mode for performing subjective examination for one eye in the binocular open state.

The fifth subjective optometry apparatus is the third subjective optometry apparatus in which the controller displays the determination information on a display.

The sixth subjective optometry apparatus is the fourth subjective optometry apparatus in which the controller displays the determination information on a display.

The seventh subjective optometry apparatus is the first subjective optometry apparatus further including an anterior segment acquisitor configured to acquire an anterior segment image of at least one of the examinee's right and left eyes, the acquisitor analyzing the anterior segment image to acquire the position information.

The eighth subjective optometry apparatus is the seventh subjective optometry apparatus in which the anterior segment acquisitor acquires, as the anterior segment image, a first anterior segment image of at least one of the examinee's right and left eyes in a case where the other eye is in an uncovered state, and acquires a second anterior segment image of at least one of the examinee's right and left eyes in a case where the other eye is in a covered state, and the acquisitor analyzes the first anterior segment image and the second anterior segment image to acquire the position information.

The ninth subjective optometry apparatus is the seventh subjective optometry apparatus in which the acquisitor performs analysis processing for the anterior segment image, thereby detecting the pupil position of the examinee's eye and acquiring the position information based on the pupil position.

The tenth subjective optometry apparatus is the eighth subjective optometry apparatus in which the acquisitor performs analysis processing for the anterior segment image, thereby detecting the pupil position of the examinee's eye and acquiring the position information based on the pupil position.

The eleventh subjective optometry apparatus is the first subjective optometry apparatus in which the corrective optical system has a right-left pair of an examinee's right-eye corrective optical system and an examinee's left-eye corrective optical system; the examinee's right-eye corrective optical system and the examinee's left-eye corrective optical system can be each position-adjusted to the examinee's eyes; and the acquisitor detects at least any one of first position information when the examinee's right-eye corrective optical system is position-adjusted to the right examinee's eye and second position information when the examinee's left-eye corrective optical system is position-adjusted to the left examinee's eye, and acquires the position information based on at least any of the first position information and the second position information.

The first subjective optometry program is a subjective optometry program used in a subjective optometry apparatus configured to subjectively measure optical characteristics of an examinee's eye, the subjective optometry apparatus including a subjective measurer which has a corrective optical system disposed on an optical path of a light projecting optical system configured to project a target light flux toward the examinee's eye and configured to change optical characteristics of the target light flux and which is configured to subjectively measure the optical characteristics of the examinee's eye. The subjective optometry program is executed by a processor of the subjective optometry apparatus, thereby causing the subjective optometry apparatus to execute the acquisition step of acquiring position information on at least one of the examinee's right and left eyes, the determination step of determining, based on the position information acquired by the acquisition step, availability of binocular fusion by the examinee's right and left eyes to acquire determination information, and the outputting step of outputting the determination information acquired by the determination step.

The first subjective optometry method is the subjective optometry method for subjectively measuring optical characteristics of an examinee's eye, the subjective optometry method including the subjective measurement step of subjectively measuring the optical characteristics of the examinee's eye by means of a corrective optical system disposed on an optical path of a light projecting optical system configured to project a target light flux toward the examinee's eye and configured to change optical characteristics of the target light flux, the acquisition step of acquiring position information on at least one of the examinee's right and left eyes, the determination step of determining, based on the position information acquired by the acquisition step, availability of binocular fusion by the examinee's right and left eyes to acquire determination information, and the outputting step of outputting the determination information acquired by the determination step.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A subjective optometry apparatus comprising:

a subjective measurer which has a corrective optical system disposed on an optical path of a light projecting optical system configured to project a target light flux toward an examinee's eye and configured to change an optical characteristic of the target light flux and which is configured to subjectively measure an optical characteristic of the examinee's eye, the corrective optical system having a right-left pair of an examinee's right-eye corrective optical system and an examinee's left-eye corrective optical system, the examinee's right-eye corrective optical system and the examinee's left-eye corrective optical system being configured to be position-adjusted to the examinee's right and left eyes, respectively;

an acquisitor configured to detect at least any one of first position information as position information on the examinee's right-eye corrective optical system obtained when the examinee's right-eye corrective optical system is position-adjusted to the right examinee's eye and second position information as position information on the examinee's left-eye corrective optical system obtained when the examinee's left-eye corrective optical system is position-adjusted to the left examinee's eye, and acquire position information on at least one of examinee's right and left eyes based on at least any of the detected first position information and the detected second position information;

a determiner configured to determine, based on the position information acquired by the acquisitor, whether or not subjective measurement can be implemented in a binocular open state of the examinee's right and left eyes, thereby acquiring determination information;

a determination information output unit configured to output the determination information acquired by the determiner;

a setter configured to receive the determination information output by the determination information output unit and set, based on the determination information, a measurement mode either to a covering mode for performing subjective examination for one of the examinee's right and left eyes with the other eye being covered or to a binocular open mode for performing subjective examination for one eye in the binocular open state; and a drive controller configured to control the subjective measurer in accordance with the measurement mode set by the setter.

2. The subjective optometry apparatus according to claim 1, wherein the determiner acquires a determination result as the determination information.

3. The subjective optometry apparatus according to claim 1, wherein the determiner is configured to acquire guide information as the determination information, and the guide information is information for guiding an examiner to the measurement mode of either the covering mode for performing subjective examination for one of the examinee's right and left eyes with the other eye being covered or the binocular open mode for performing subjective examination for one eye in the binocular open state.

4. The subjective optometry apparatus according to claim 2, wherein the determination information output unit displays the determination information on a display.

5. The subjective optometry apparatus according to claim 3, wherein the determination information output unit displays the determination information on a display.

6. The subjective optometry apparatus according to claim 1, further comprising:

an anterior segment acquisitor configured to acquire an anterior segment image of at least one of the examinee's right and left eyes, wherein the acquisitor acquires the position information by analyzing the anterior segment image.

7. The subjective optometry apparatus according to claim 6, wherein the anterior segment acquisitor acquires a first anterior segment image as the anterior segment image of at least one of the examinee's right and left eyes in a case where both of the examinee's right and left eyes are in an uncovered state, and acquires a second anterior segment image as the anterior segment image of at least one of the examinee's right and left eyes in a case where the other eye is in a covered state, and the acquisitor acquires the position information by analyzing the first anterior segment image and the second anterior segment image.

8. The subjective optometry apparatus according to claim 6, wherein the acquisitor detects a pupil position of the examinee's eye by performing analysis processing for the anterior segment image and acquires the position information based on the pupil position.

9. The subjective optometry apparatus according to claim 7, wherein the acquisitor detects a pupil position of the examinee's eye by performing analysis processing for the anterior segment image and acquires the position information based on the pupil position.

10. A non-transitory recording medium storing a subjective optometry program for a subjective optometry apparatus, the subjective optometry apparatus including a subjective measurer which has a corrective optical system disposed on an optical path of a light projecting optical system configured to project a target light flux toward an examinee's eye and configured to change an optical characteristic of the target light flux and which is configured to subjectively measure an optical characteristic of the examinee's eye, the corrective optical system having a right-left pair of an examinee's right-eye corrective optical system and an examinee's left-eye corrective optical system, the examinee's right-eye corrective optical system and the examinee's left-eye corrective optical system being configured to be position-adjusted to the examinee's right and left eyes, respectively, the subjective optometry program being executed by a processor of a-the subjective optometry apparatus to cause the subjective optometry apparatus to execute detecting at least any one of first position information as position information on the examinee's right-eye corrective optical system obtained when the examinee's right-eye corrective optical system is position-adjusted to the right examinee's eye and second position information as position information on the examinee's left-eye corrective optical system obtained when the examinee's left-eye corrective optical system is position-adjusted to the left examinee's eye, acquiring position information on at least one of examinee's right and left eyes based on at least any of the detected first position information and the detected second position information, determining, based on the position information, availability of binocular fusion by the examinee's right and left eyes to acquire determination information, outputting the determination information, receiving the determination information, setting, based on the determination information, a measurement mode either to a covering mode for performing subjective examination for one of the examinee's right and left eyes with the other eye being covered or to a binocular open mode for performing subjective examination for one eye in the binocular open state, and controlling the subjective measurer in accordance with the set measurement mode.

11. A subjective optometry method comprising:

providing a subjective measurer which has a corrective optical system disposed on an optical path of a light projecting optical system configured to project a target light flux toward an examinee's eye and configured to change an optical characteristic of the target light flux and which is configured to subjectively measure an optical characteristic of the examinee's eye, the corrective optical system having a right-left pair of an examinee's right-eye corrective optical system and an examinee's left-eye corrective optical system, the examinee's right-eye corrective optical system and the examinee's left-eye corrective optical system being configured to be position-adjusted to the examinee's right and left eyes, respectively;

detecting at least any one of first position information as position information on the examinee's right-eye corrective optical system obtained when the examinee's right-eye corrective optical system is position-adjusted to the right examinee's eye and second position information as position information on the examinee's left-eye corrective optical system obtained when the examinee's left-eye corrective optical system is position-adjusted to the left examinee's eye;

acquiring position information on at least one of examinee's right and left eyes based on at least any of the detected first position information and the detected second position information;

determining, based on the position information, availability of binocular fusion by the examinee's right and left eyes to acquire determination information;

outputting the determination information;

receiving the determination information;

setting, based on the determination information, a measurement mode either to a covering mode for performing subjective examination for one of the examinee's right and left eyes with the other eye being covered or to a binocular open mode for performing subjective examination for one eye in the binocular open state;

controlling the subjective measurer in accordance with the set measurement mode; and subjectively measuring an optical characteristic of each of the examinee's eyes.

12. The subjective optometry apparatus according to claim 1, wherein the binocular open state of the examinee's right and left eyes is a state in which both of the examinee's right and left eyes are uncovered.

13. The subjective optometry apparatus according to claim 1, wherein one of the examinee's right and left eyes includes a particular portion to be detected, the position information includes first and second positions of the particular portion, the first position being detected when both of the examinee's right and left eyes are uncovered, the second position being detected when the one of the examinee's right and left eyes is uncovered while another of the examinee's right and left eyes is covered.

14. The subjective optometry apparatus according to claim 1, wherein the determiner determines whether or not the subjective measurement can be implemented in a binocular open state of the examinee's right and left eyes by determining whether or not binocular fusion can be performed by the examinee's right and left eyes.

15. The subjective optometry apparatus according to claim 13, wherein the determiner is configured to:

determine, based on the first and second positions, an amount of movement of the particular portion in the one of the examinee's right and left eyes, determine whether the amount of movement exceeds a preset threshold, determine the subjective measurement can be implemented in the binocular open state of the examinee's right and left eyes when the amount of movement falls within the preset threshold; and determine the subjective measurement cannot be implemented in the binocular open state of the examinee's right and left eyes when the amount of movement exceeds the preset threshold.

16. The subjective optometry apparatus according to claim 1, wherein the subjective measurement in the binocular open state of the examinee's right and left eyes is performed in a state in which (i) both of the examinee's right and left eyes are uncovered and a positive spherical power is added for one of the examinee's right and left eyes; or (ii) both of the examinee's right and left eyes are uncovered and a deflecting mirror is used for one of the examinee's right and left eyes.

* * * * *